(12) United States Patent
Maeda et al.

(10) Patent No.: US 7,784,942 B2
(45) Date of Patent: Aug. 31, 2010

(54) FUNDUS OCULI OBSERVATION DEVICE, A FUNDUS OCULI IMAGE DISPLAY DEVICE AND A FUNDUS OCULI IMAGE DISPLAY METHOD

(75) Inventors: Naoyuki Maeda, Osaka (JP); Kazuhiko Yumikake, Tokyo (JP); Takashi Shioiri, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 237 days.

(21) Appl. No.: 11/866,529

(22) Filed: Oct. 3, 2007

(65) Prior Publication Data

US 2008/0084538 A1 Apr. 10, 2008

(30) Foreign Application Priority Data

Oct. 4, 2006 (JP) .............................. 2006-273444

(51) Int. Cl.
*A61B 3/10* (2006.01)
*A61B 3/14* (2006.01)

(52) U.S. Cl. ..................... 351/206; 351/205; 351/221

(58) Field of Classification Search .......... 351/200–246
See application file for complete search history.

(56) References Cited

U.S. PATENT DOCUMENTS

| 6,179,421 | B1 | 1/2001 | Pang | 351/205 |
|---|---|---|---|---|
| 6,788,421 | B2 | 9/2004 | Fercher et al. | 356/497 |
| 7,245,383 | B2 | 7/2007 | Chan et al. | 356/497 |
| 7,566,128 | B2 * | 7/2009 | Tsukada et al. | 351/205 |
| 2003/0053072 | A1 | 3/2003 | Fercher et al. | |
| 2004/0036838 | A1* | 2/2004 | Podoleanu et al. | 351/206 |
| 2005/0190374 | A1 | 9/2005 | Chan et al. | |
| 2006/0187462 | A1 | 8/2006 | Srinivasan et al. | |

FOREIGN PATENT DOCUMENTS

| JP | 7-178056 | 7/1995 |
|---|---|---|
| JP | 2001-521422 | 11/2001 |
| JP | 2003000543 | 7/2003 |
| JP | 2004350849 | 12/2004 |

(Continued)

OTHER PUBLICATIONS

European Search Report mailed May 30, 2008, issued on the corresponding European patent application No. 07019352.9.

(Continued)

*Primary Examiner*—Mohammed Hasan
(74) *Attorney, Agent, or Firm*—Edwards Angell Palmer & Dodge LLP

(57) ABSTRACT

A fundus oculi observation device comprises: a first image forming part for optically obtaining data and then forming a fluorescence image of a fundus oculi of an eye administered with a fluorescent agent in advance based on the obtained data; a second image forming part for optically obtaining data and then forming a tomographic image of the fundus oculi based on the obtained data; a display; and a controller for causing said display to display said fluorescence image formed by said first image forming part side-by-side with said tomographic image formed by said second image forming part, as well as to display cross-sectional position information that represents a cross-sectional position of said tomographic image in said fluorescence image by overlapping it with said fluorescent image.

15 Claims, 17 Drawing Sheets

FOREIGN PATENT DOCUMENTS

| | | |
|---|---|---|
| JP | 2005241464 | 9/2005 |
| JP | 2006-212153 | 8/2006 |

OTHER PUBLICATIONS

R. B. Rosen et al., "Simultaneous OCT/SLO/ICG system," Proc. of SPIE, vol. 6079, Feb. 20, 2006, pp. 60790A-1-60790A-6.

S. Jiao et al., "Simultaneous acquisition of sectional and fundus ophthalmic images with spectral-domain optical coherence tomography," Optics Express, vol. 13, No. 2, Jan. 24, 2005, pp. 444-452.

R. B. Rosen et al., "A Prototype Instrument for Simultaneous Indocyanine Green (ICG) Angiography and Multi-planar Optical Coherence Tomography (OCT) Imaging of the Retina," IOVS, vol. 45, Apr. 2004, p. U931 (2 sheets).

G.M. Dobre et al., "Simultaneous optical coherence tomography-Indocyanine Green dye fluorescence imaging system for investigations of the eye's fundus," Optical Letters, vol. 30, No. 1, Jan. 2005, pp. 58-60.

International Search Report and Written Opinion mailed Jan. 15, 2008, issued in International Application No. PCT/JP2007/069490.

* cited by examiner

PRIOR ART

PRIOR ART

FUNDUS OCULI OBSERVATION DEVICE, A FUNDUS OCULI IMAGE DISPLAY DEVICE AND A FUNDUS OCULI IMAGE DISPLAY METHOD

BACKGROUND OF THE INVENTION

1. Field of the Invention

The present invention relates to a fundus oculi observation device, a fundus oculi image display device and a fundus oculi image display method that are used for observing the state of the fundus oculi of an eye.

2. Description of the Related Art

As a fundus oculi observation device, conventionally, a retinal camera has been widely used. FIG. 16 shows one example of the appearance of a conventional, general retinal camera, and FIG. 17 shows one example of an optical system configuration internally accommodated in the retinal camera (e.g. JP Patent laid-open No. 2004-350849). Herein, "observation" includes at least a case of observing produced fundus oculi images (observation of a fundus oculi with a naked eye may be included).

First, referring to FIG. 16, an explanation will be made regarding the appearance of a conventional retinal camera 5000. This retinal camera 5000 is provided with a platform 3 mounted on a base 2 so as to be slidable in the front and rear, right and left directions (horizontal direction). On this platform 3, an operation panel and a control lever 4 are installed for an examiner to conduct various operations.

The examiner can freely move the platform 3 on the base 2 by operating the control lever 4. On the top of the control lever 4, an operation button 4a that is pressed down for requiring execution of production of fundus oculi images is installed.

On the base 2, a post 5 is installed standing upwards. On this post 5, a jaw rest 6 where the jaw of a patient is rested and an external fixation lamp 7 that is a light source for fixing an eye E are provided.

On the platform 3, a main body part 8 is installed to accommodate various optical systems and control systems of the retinal camera 5000. The control system may be installed, for example, inside the base 2 or the platform 3, or in an external device such as a computer connected to the retinal camera 5000.

On the side of an eye E of the main body part 8, an objective lens part 8a disposed facing the eye E is installed. On the examiner's side, an eyepiece part 8b is installed.

Further, to the main body part 8, a still camera 9 for producing a still image of the fundus oculi of the eye E and an imaging device 10 such as a TV camera for producing still images or moving images of the fundus oculi are connected. The still camera 9 and the imaging device 10 are formed so as to be removable from the main body part 8.

As the still camera 9, in accordance with various conditions such as the purpose of an examination and the saving method of produced images, a digital camera equipped with a CCD, a film camera and an instant camera may interchangeably be used appropriately. The main body part 8 is equipped with a mounting part 8c for interchangeably mounting the still camera 9.

In a case where the still camera 9 and the imaging device 10 are for taking digital images, it is possible to transmit and store image data into an image recording device such as a computer connected to the retinal camera 5000.

Furthermore, on the examiner's side of the main body part 8, a touch panel monitor 11 is installed. On this touch panel monitor 11, a fundus oculi image of the eye E formed based on video signals outputted from the (digital-type) still camera 9 or imaging device 10 is displayed. Moreover, on the touch panel monitor 11, an x-y coordinate system taking the center of a screen as the origin is displayed overlapped with the fundus oculi image. When the examiner touches the screen, a coordinate value corresponding to a touched position is displayed.

Next, referring to FIG. 17, a configuration of an optical system of the retinal camera 5000 will be described. The retinal camera 5000 is provided with an illumination optical system 100 that lights the fundus oculi Ef of the eye E, and an imaging optical system 120 that guides the illumination light reflected by the fundus oculi to the eyepiece part 8b, the still camera 9 and the imaging device 10.

The illumination optical system 100 comprises: a halogen lamp 101; a condenser lens 102; a xenon lamp 103; a condenser lens 104; exciter filters 105 and 106; a ring transparent plate 107; a mirror 108; an LCD 109; an illumination diaphragm 110; a relay lens 111; an aperture mirror 112; and an objective lens 113.

The halogen lamp 101 is an observation light source that emits continuous light. The condenser lens 102 is an optical element for converging the continuous light (observation illumination light) emitted by the halogen lamp 101 and evenly applying the observation illumination light to the eye E (fundus oculi Ef).

The xenon lamp 103 is an imaging light source that is flashed at the time of imaging of fundus oculi Ef. The condenser lens 104 is an optical element for converging the flash light (imaging illumination light) emitted by the xenon lamp 103 and evenly applying the imaging illumination light to the fundus oculi Ef.

The exciter filters 105 and 106 are filters used at the time of fluorography of images of the fundus oculi Ef. The exciter filters 105 and 106 can be respectively inserted into and removed from an optical path by a drive mechanism such as a solenoid. The exciter filter 105 is placed on the optical path at the time of FAG (fluorescein angiography). The exciter filter 106 is placed on the optical path at the time of ICG (indocyanine green angiography). Hereinafter, an image showing the state of the fundus oculi (blood vessels) of the eye to which a fluorescence agent has been administered will be generically referred to as a "fluorescence image." At the time of color-imaging, both the exciter filters 105 and 106 are retracted from the optical path.

The ring transparent plate 107 is placed in a conjugating location with a pupil of the eye E, and is equipped with a ring transparent part 107a taking the optical axis of the illumination optical system 100 as the center. The mirror 108 reflects the illumination light emitted by the halogen lamp 101 or the xenon lamp 103, in a direction of the optical axis of the imaging optical system 120. The LCD 109 displays a fixation target (not illustrated) for fixing the eye E.

The illumination diaphragm 110 is a diaphragm member to shut out part of the illumination light in order to prevent flare, etc. This illumination diaphragm 110 is composed so as to be movable in the light axis direction of the illumination optical system 100, and is thus capable of changing an illumination region of the fundus oculi Ef.

The aperture mirror 112 is an optical element that combines the optical axis of the illumination optical system 100 and the optical axis of the imaging optical system 120. In the center region of the aperture mirror 112, an aperture 112a is opened. The optical axis of the illumination optical system 100 and the optical axis of the imaging optical system 120 cross each other at a substantially central location of this aperture 112a. The objective lens 113 is installed in the objective lens part 8a of the main body part 8.

The illumination optical system 100 having such a configuration illuminates the fundus oculi Ef in the following manner. First, at the time of fundus oculi observation, the halogen lamp 101 is turned on and the observation illumination light is emitted. This observation illumination light is applied to the ring transparent plate 107 through the condenser lenses 102 and 104. The light passed through the ring transparent part 107a of the ring transparent plate 107 is reflected by the mirror 108, and after passing through the LCD 109, the illumination diaphragm 110 and the relay lens 111, reflected by the aperture mirror 112 so as to be along the optical axis direction of the imaging optical system 120. Then, the light is converged by the objective lens 113 to enter the eye E, thereby illuminating the fundus oculi Ef.

At this moment, since the ring transparent plate 107 is placed in a conjugating location with the pupil of the eye E, a ring-shaped image of the observation illumination light entering the eye E is formed on the pupil. The entering fundus oculi reflection light of the observation illumination light is emitted from the eye E through a central dark part of the ring-shaped image on the pupil.

On the other hand, at the time of imaging of the fundus oculi Ef, flush light is emitted from the xenon lamp 103, and the imaging illumination light is applied to the fundus oculi Ef through the same path. In the case of fluorography, either the exciter filter 105 or the exciter filter 106 is selectively placed on the optical path, depending on whether FAG imaging or ICG imaging is carried out.

The imaging optical system 120 comprises: an objective lens 113; an aperture mirror 112 (an aperture 112a thereof); an imaging diaphragm 121; barrier filters 122 and 123; a variable magnifying lens 124; a relay lens 125; an imaging lens 126; a quick return mirror 127; and an imaging media 9a. Herein, the imaging media 9a is an imaging media (CCD, camera film, instant film, etc.) for the still camera 9.

The fundus oculi reflection light of the illumination light exiting through the central dark part of the ring-shaped image formed on the pupil of the eye E enters the imaging diaphragm 121 through the aperture 112a of the aperture mirror 112. The aperture mirror 112 reflects cornea reflection light of the illumination light, and acts so as not to mix the cornea reflection light into the fundus oculi reflection light entering the imaging diaphragm 121. As a result, generation of flare on the observation images and produced images is prevented.

The imaging diaphragm 121 is a plate-shaped member having a plurality of circular light-transmitting parts of different sizes. The plurality of light-transmitting parts compose diaphragms with different diaphragm values (F value), and are placed alternatively on the optical path by a drive mechanism (not illustrated herein).

The barrier filters 122 and 123 can be inserted into and removed from the optical path by a drive mechanism such as a solenoid. In the event of FAG imaging, the barrier filter 122 is placed on the optical path, whereas in the event of ICG imaging, the barrier filter 123 is placed on the optical path. Further, at the time of color-imaging, both the barrier filters 122 and 123 are retracted from the optical path.

The variable magnifying lens 124 is movable in the optical axis direction of the imaging optical system 120 by a drive mechanism (not illustrated herein). This makes it possible to change an observation magnifying ratio and an imaging magnifying ratio, and to focus images of the fundus oculi. The imaging lens 126 is a lens that focuses the fundus oculi reflection light from the eye E onto the imaging media 9a.

The quick return mirror 127 is disposed so as to be capable of being rotated around a rotary shaft 127a by a drive mechanism (not illustrated herein). In a case where imaging of the fundus oculi Ef is performed with the still camera 9, the fundus oculi reflection light is guided to the imaging media 9a by springing up the quick return mirror 127 that is obliquely mounted on the optical path. Meanwhile, in a case where imaging of the fundus oculi is performed with the imaging device 10, or in a case where observation of the fundus oculi is performed with the naked eye of the examiner, the quick return mirror 127 is obliquely mounted on the optical path to upwardly reflect the fundus oculi reflection light.

For guiding the fundus oculi reflection light reflected by the quick return mirror 127, the imaging optical system 120 is further provided with a field lens 128, a switching mirror 129, an eyepiece 130, a relay lens 131, a reflection mirror 132, an imaging lens 133, and an image pick-up element 10a. The image pick-up element 10a is an image pick-up element such as a CCD installed in the imaging device 10. On the touch panel monitor 11, a fundus oculi image Ef imaged by the image pick-up element 10a is displayed.

The switching mirror 129 is rotatable around a rotary shaft 129a in the same manner as the quick return mirror 127. This switching mirror 129 is obliquely disposed on the optical path during observation with the naked eye, thereby reflecting and guiding the fundus oculi reflection light to the eyepiece 130.

When a fundus oculi image is imaged by the imaging device 10, the switching mirror 129 is retracted from the optical path. The fundus oculi reflection light is focused onto the image pick-up element 10a via the relay lens 131, the mirror 132 and the imaging lens 133, and the fundus oculi image Ef' is displayed on the touch panel monitor 11.

The retinal camera 5000 is a fundus oculi observation device used for observing the state of the surface of a fundus oculi Ef, that is, the surface of the retina. On the other hand, in the deep layer of retina, tissues such as the choroidea and sclera exist. In recent years, a device for observing these deep-layer tissues has been practically implemented (e.g. JP Patent laid-open No. 2003-00543, and JP Patent laid-open No. 2004-52915).

Each of the fundus oculi observation devices disclosed in JP Patent laid-open No. 2003-00543 and JP Patent laid-open No. 2004-52915 is a device (referred to as an optical image measurement device, an optical coherence tomography device, and the like) to which a so-called OCT (Optical Coherence Tomography) technology is applied. Such a fundus oculi observation device is a device that splits low-coherence light into two, guides one (signal light) of the lights to the fundus oculi and the other (reference light) to a given reference object and, based on interference light obtained by overlaying the signal light passed through the fundus oculi and the reference light reflected by the reference object, forms tomographic images of the surface and deep layer tissue of the fundus oculi.

In order to ascertain, in detail, the condition of the fundus oculi (such as the presence or absence of a disorder, stages of progression of a disorder, the degree of therapeutic effect, and the recovery condition), it is regarded as desirable to consider the condition of the surface of the fundus oculi (surface of the retina) and the vicinity thereof (a shallow region under the surface of the retina) and the condition of deeper tissues of the fundus oculi (such as deep tissues of the retina, choroids, and sclera).

However, a retinal camera is a device for obtaining images of the surface of the fundus oculi (such as a color image and a fluorescein fluorescence image), and images of vicinity of the surface of the fundus oculi (such as an indocyanine green fluorescence image). Therefore, it is difficult to ascertain, in detail, the condition of deeper tissues of the fundus oculi, by merely observing an image obtained with a retinal camera. In addition, a considerable amount of skill is required for interpretation, because information overlapping in the depth direction of the fundus oculi is obtained.

Meanwhile, an optical image measurement device is a device for obtaining the tomographic image of the fundus oculi, so that it is difficult to ascertain, in detail, the condition of the surface of the fundus oculi and the vicinity thereof, by merely observing an image obtained with an optical image measurement device. In particular, an image obtained with a so-called Fourier domain optical image measurement device is a tomographic image having a cross section in the depth direction of the fundus oculi, so that it is difficult to ascertain, in detail, the condition of the fundus oculi in a direction of the surface of the fundus oculi.

In addition, in order to comprehensively assess the condition of the fundus oculi, it is regarded as desirable to assess the state of a disease or the like by considering the condition of the surface of the fundus oculi and the vicinity thereof as well as the condition of deeper tissues.

For example, in diagnoses of age-related macular degeneration, newly formed ressels in a choroidal, etc., a fluorescence image of the fundus oculi is useful for observation of the condition of a blood vessel on the surface of the fundus oculi or the vicinity thereof (particularly, comprehension of a leakage condition that cannot be observed on a tomographic image by the optical image measurement device), and a tomographic image by the optical image measurement device is useful in the observation of the condition of a cross section of a retina or a choroid.

In order to enable the diagnoses as described above, it is necessary to present an image obtained by the retinal camera and an image obtained by the optical image measurement device in a display form in which they can be compared with each other. For example, it is desirable to facilitate the comparative work by presenting both the images simultaneously.

In addition, it is desirable to adopt a display form in which the mutual relationship between the image from the retinal camera and the image from the optical image measurement device can be easily ascertained, making it possible to easily perform the comparative work.

In particular, when a site of interest such as an involved are a is specified on one image, it is often desirable to ascertain the condition of the site of interest in more detail by referring to the condition of the site of interest on another image.

However, conventional fundus oculi observation devices cannot easily clarify the mutual positional relationship between an image of the surface of the fundus oculi and the vicinity thereof by the retinal camera and a tomographic image of the fundus oculi from the optical image measurement device, so that it is difficult to ascertain, in detail, the condition of a site of interest.

SUMMARY OF THE INVENTION

The present invention has been achieved in order to solve these problems, and an object thereof is to provide a fundus oculi observation device, a fundus oculi image display device, and a fundus oculi image display method, that are capable of ascertaining, in detail, the condition of the surface of the fundus oculi of the eye and the vicinity thereof, and the condition of deeper tissues.

In order to achieve the aforementioned object, in a first aspect of the present invention, a fundus oculi observation device comprises: a first image forming part configured to optically obtain data and, based on the obtained data, form a fluorescence image of a fundus oculi of an eye administered with a fluorescent agent in advance; a second image forming part configured to optically obtain data and, based on the obtained data, form a tomographic image of the fundus oculi; a display part; and a controller configured to cause the display part to display the fluorescence image formed by the first image forming part side by side with the tomographic image formed by the second image forming part, and display cross-sectional-position information that represents a cross-sectional position of the tomographic image in the fluorescence image so as to overlap the fluorescent image.

In a second aspect of the present invention, the first image forming part forms a fluorescein fluorescence image as the fluorescence image In a third aspect of the present invention, the first image forming part forms an indocyanine green fluorescence image as the fluorescence image.

In a fourth aspect of the present invention, the fundus oculi observation device further comprises: a cross-sectional-pattern designating part configured to designate a cross-sectional pattern of a tomographic image of a fundus oculi, wherein: the second image forming part forms one or more tomographic images based on the designated cross-sectional pattern; and the controller causes the formed one or more tomographic images to be displayed side by side with the fluorescence image, and causes the cross-sectional-position information of each of the one or more tomographic images to be displayed so as to overlap the fluorescence image.

In a fifth aspect of the invention, the fundus oculi observation device further comprises: a cross-sectional-pattern designating part configured to designate a cross-sectional pattern on the displayed fluorescence image; wherein the second image forming part forms the tomographic image in the designated cross-sectional position.

In a sixth aspect of the present invention, the second image forming part forms a new tomographic image in a cross-sectional position including a point on a cross-sectional position designated by the cross-sectional-position designating part, and a point on the fluorescence image equivalent to a central fossa of the fundus oculi; and the controller causes the newly formed tomographic image to be displayed side by side with the fluorescence image.

In a seventh aspect of the present invention, the controller causes a scale image representing a distance on the displayed fluorescence image and/or on the displayed tomographic image, to be displayed with the fluorescence image and/or the tomographic image.

In an eighth aspect of the present invention, the first image forming part optically obtains data and further forms a 2D image of a surface of the fundus oculi based on the obtained data, and the controller causes the display part to display the formed 2D image side by side with the fluorescence image and the tomographic image, and display cross-sectional-position information that represents a cross-sectional position of the tomographic image in the 2D image so as to overlap the 2D image.

In a ninth aspect of the present invention, the fundus oculi observation device further comprises a cross-sectional-pattern designating part configured to designate a cross-sectional pattern of a tomographic image of a fundus oculi, and is characterized in that: the second image forming part forms one or more tomographic images based on the designated cross-sectional pattern; and the controller causes the formed one or more tomographic images to be displayed side by side with the fluorescence image and the 2D image, and causes the cross-sectional-position information of each of the one or more tomographic images, to be displayed so as to overlap each of the fluorescence image and the 2D image.

In a tenth aspect of the present invention, the fundus oculi observation device further comprises a cross-sectional-position designating part configured to designate a cross-sectional position on the displayed 2D image, and is characterized in that the second image forming part forms a tomographic image in the designated cross-sectional position.

In an eleventh aspect of the present invention, the second image forming part forms a new tomographic image in a cross-sectional position including a point on a cross-sectional position designated by the cross-sectional-position designating part, and a point on the 2D image corresponding to a central fossa of the fundus oculi, and the controller causes the newly formed tomographic image to be displayed side by side with the 2D image.

In a twelfth aspect of the present invention, the controller causes a scale image representing a distance on the displayed fluorescence image, the displayed tomographic image, and/or the displayed 2D image, to be displayed with the fluorescence image, the tomographic image, and/or the 2D image.

In thirteenth aspect of the present invention, the controller comprises a display-size-changing part configured to match a display size between the fluorescence image and the 2D image, and causes the fluorescence image and the 2D image whose display sizes are matched, to be displayed side by side with the tomographic image.

In a fourteenth aspect of the present invention, the controller, in the case in which a cross-sectional pattern designated by the cross-sectional-pattern designating part has two or more cross-sectional positions that mutually cross, causes crossing-position information representing the crossing position to be displayed so as to overlap each of the tomographic images of the two or more cross-sectional positions.

In a fifteenth aspect of the present invention, the controller, in the case in which a cross-sectional pattern designated by the cross-sectional-pattern designating part has two or more cross-sectional positions that mutually cross, causes crossing-position information representing the crossing position to be displayed so as to overlap each of the tomographic images of the two or more cross-sectional positions.

In a sixteenth aspect of the present invention, a fundus oculi image display device comprises: a storage configured to store a fluorescence image of a fundus oculi of an eye and a tomographic image of the fundus oculi; a display part; and a controller for causing the display part to display the stored fluorescence image side by side with the stored tomographic image, and display cross-sectional-position information representing a cross-section position of the tomographic image in the fluorescence image side by side with the fluorescence image.

In a seventeenth aspect of the present invention, a fundus oculi image display method by a display device comprises: a storage configured to store a fluorescence image of a fundus oculi of an eye and a tomographic image of the fundus oculi; and a display, and is characterized in that the display displays the stored fluorescence image side by side with the tomographic image and displays a cross-sectional-position information representing a cross-section position for the tomographic image in the fluorescence image side by side so as to overlapping it with the fluorescence image.

According to the present embodiment, it is possible to form both a fluorescence image and a tomographic image, to display the fluorescence image and the tomographic image side by side, and to display the cross-sectional-position information that represents the cross-sectional position of a tomographic image overlapping the fluorescence image.

The fluorescence image is an image that represents the condition of the surface of a fundus oculi and the vicinity thereof. In addition, the tomographic image is an image that represents the condition of a cross section spanning from the surface of a fundus oculi to deeper tissues.

Therefore, according to the present embodiment, an examiner can observe both the fluorescence image and the tomographic image simultaneously, can further ascertain the position relationship between the fluorescence image and the tomographic image, and can thereby ascertain, in detail, the condition of the surface of the fundus oculi and the vicinity thereof as well as the condition of deeper tissues.

BRIEF DESCRIPTION OF THE DRAWINGS

FIG. 8A shows one example of the feature of scan of signal light when a fundus oculi is seen from the incident side of the signal light with respect to an eye. FIG. 8B shows one example of the feature of arrangement of scanning points on each scanning line.

DETAILED DESCRIPTION OF THE REFERENCE EMBODIMENTS

Figure 1:
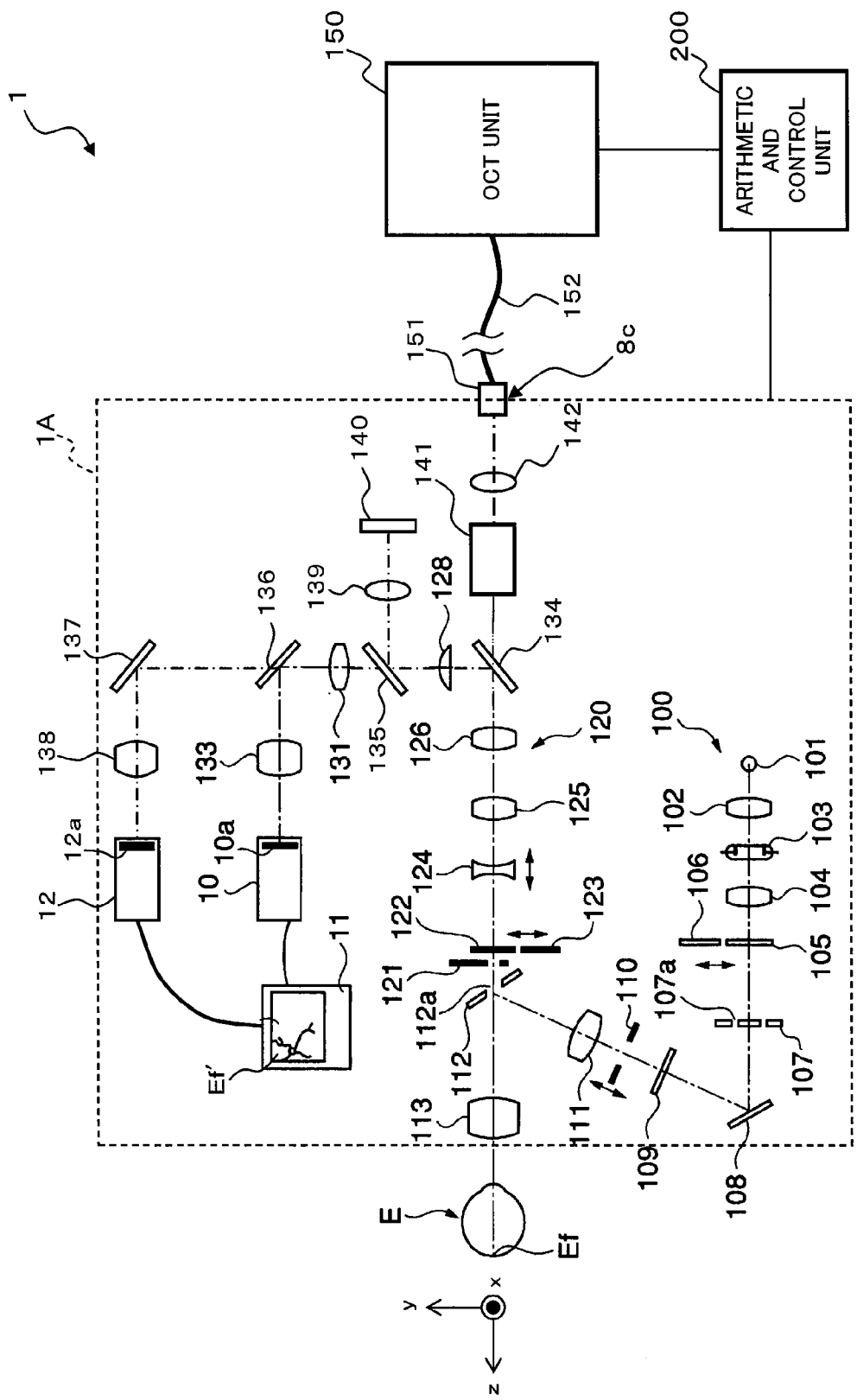
FIG. 1 is a schematic diagram showing one example of the configuration in a preferred embodiment of the fundus oculi observation device according to the present invention.

One example of preferred embodiments of a fundus oculi display device, a fundus oculi image display device and a fundus oculi image observation method according to the present invention will be described in detail referring to the drawings. For the same structural parts as the conventional ones shown in FIGS. 16 and 17, the same symbols used in these figures will be used.

Configuration of Device

Figure 2:
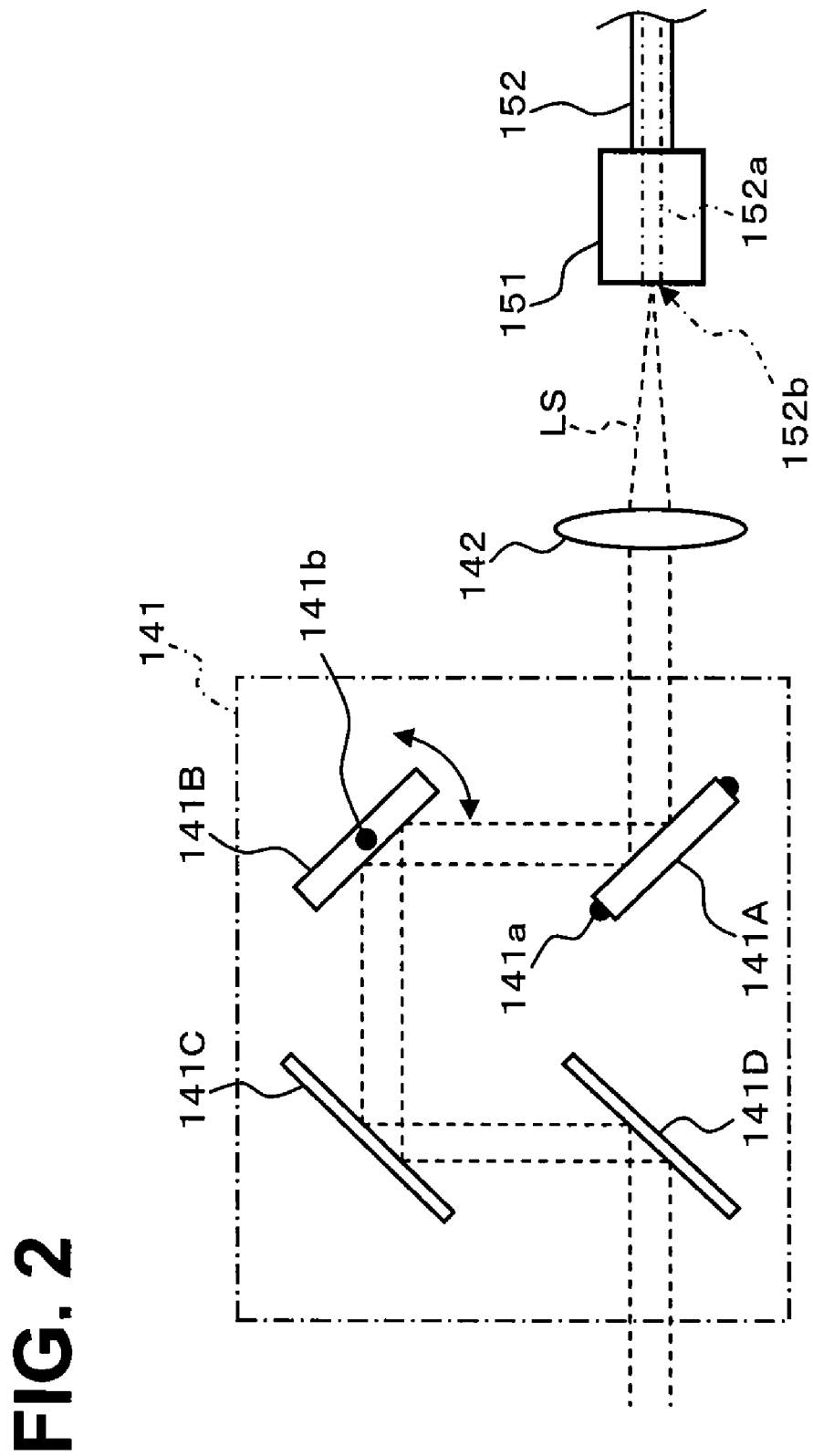
FIG. 2 is a schematic diagram showing one example of the configuration of a scanning unit installed in the retinal camera unit in the preferred embodiment of the fundus oculi observation device according to the present invention.
Figure 3:
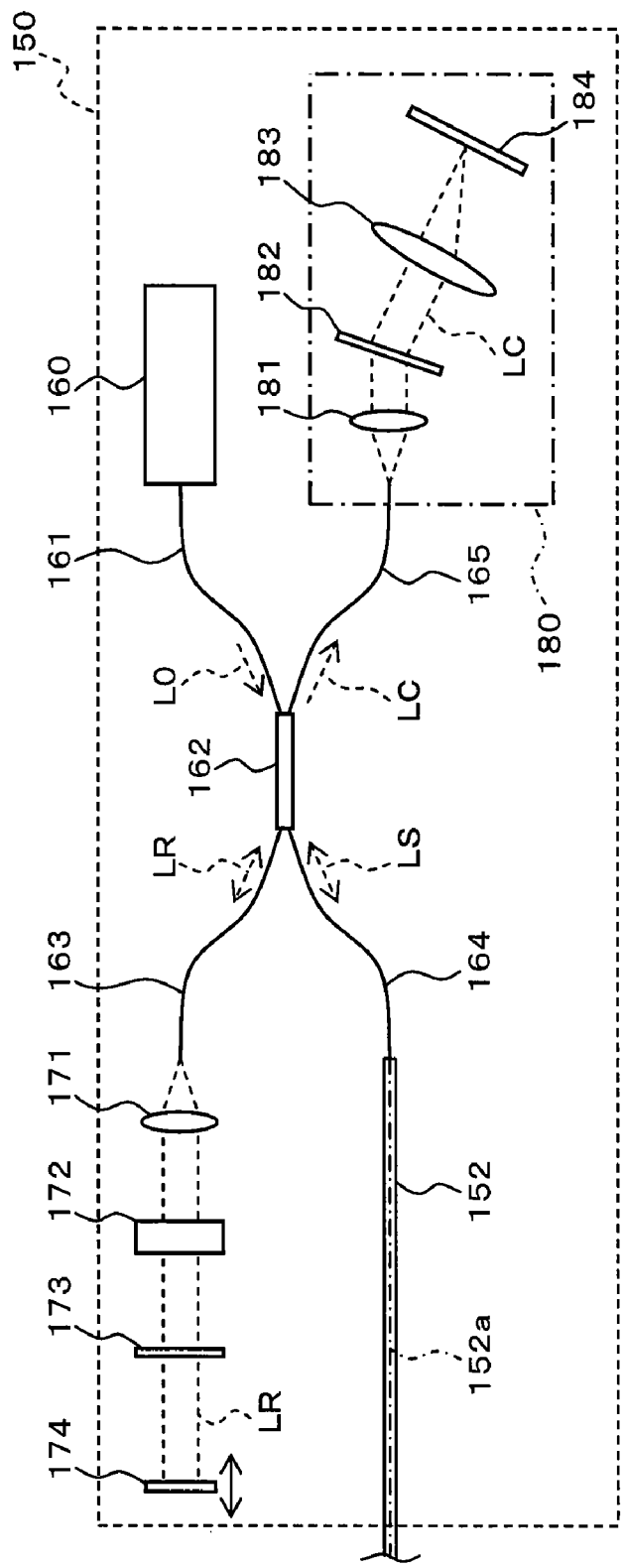
FIG. 3 is a schematic diagram showing one example of the configuration of an OCT unit in the preferred embodiment of the fundus oculi observation device according to the present invention.
Figure 4:
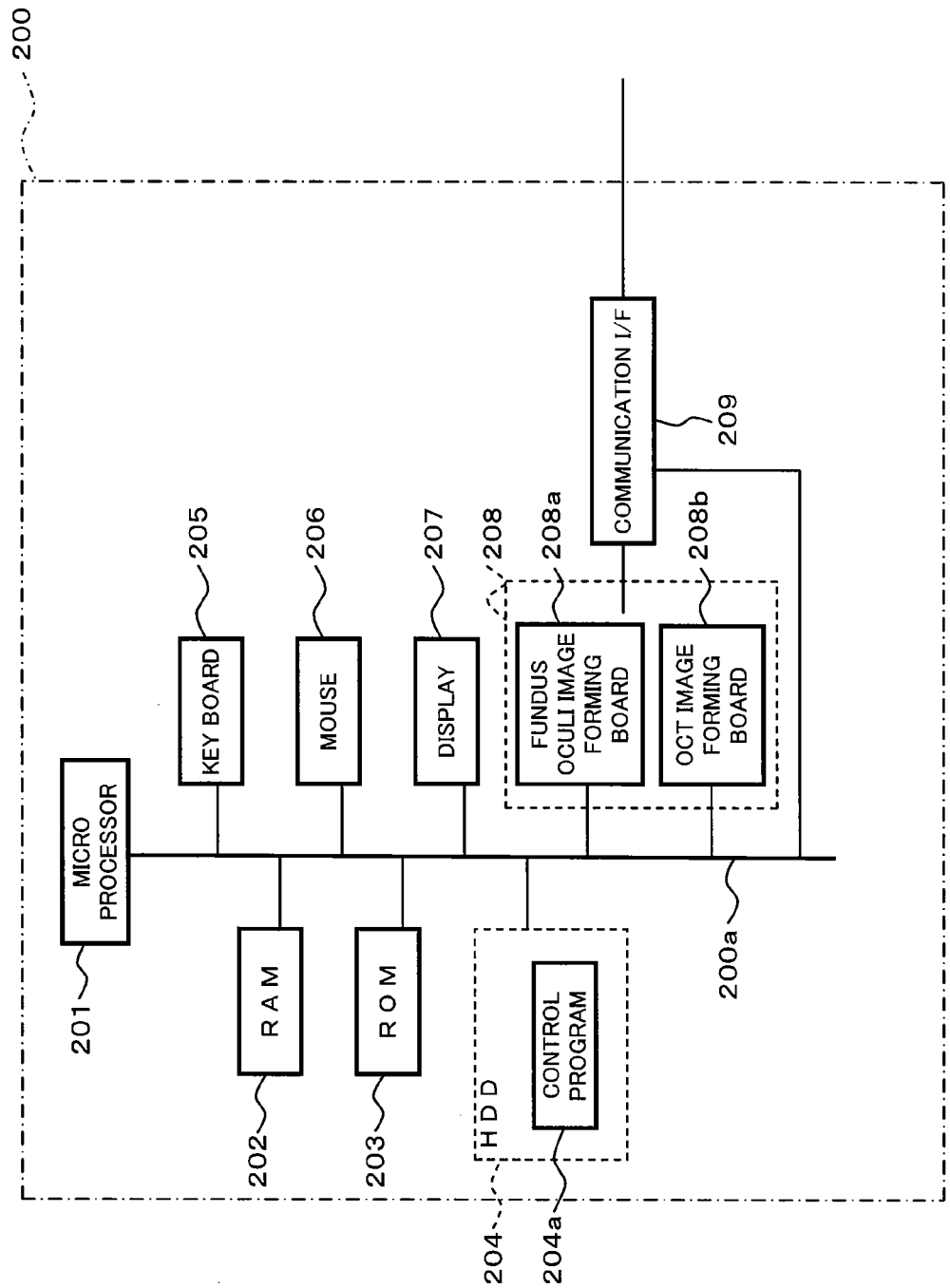
FIG. 4 is a schematic block diagram showing one example of the hardware configuration of an arithmetic and control unit in the preferred embodiment of the fundus oculi observation device according to the present invention.
Figure 5:
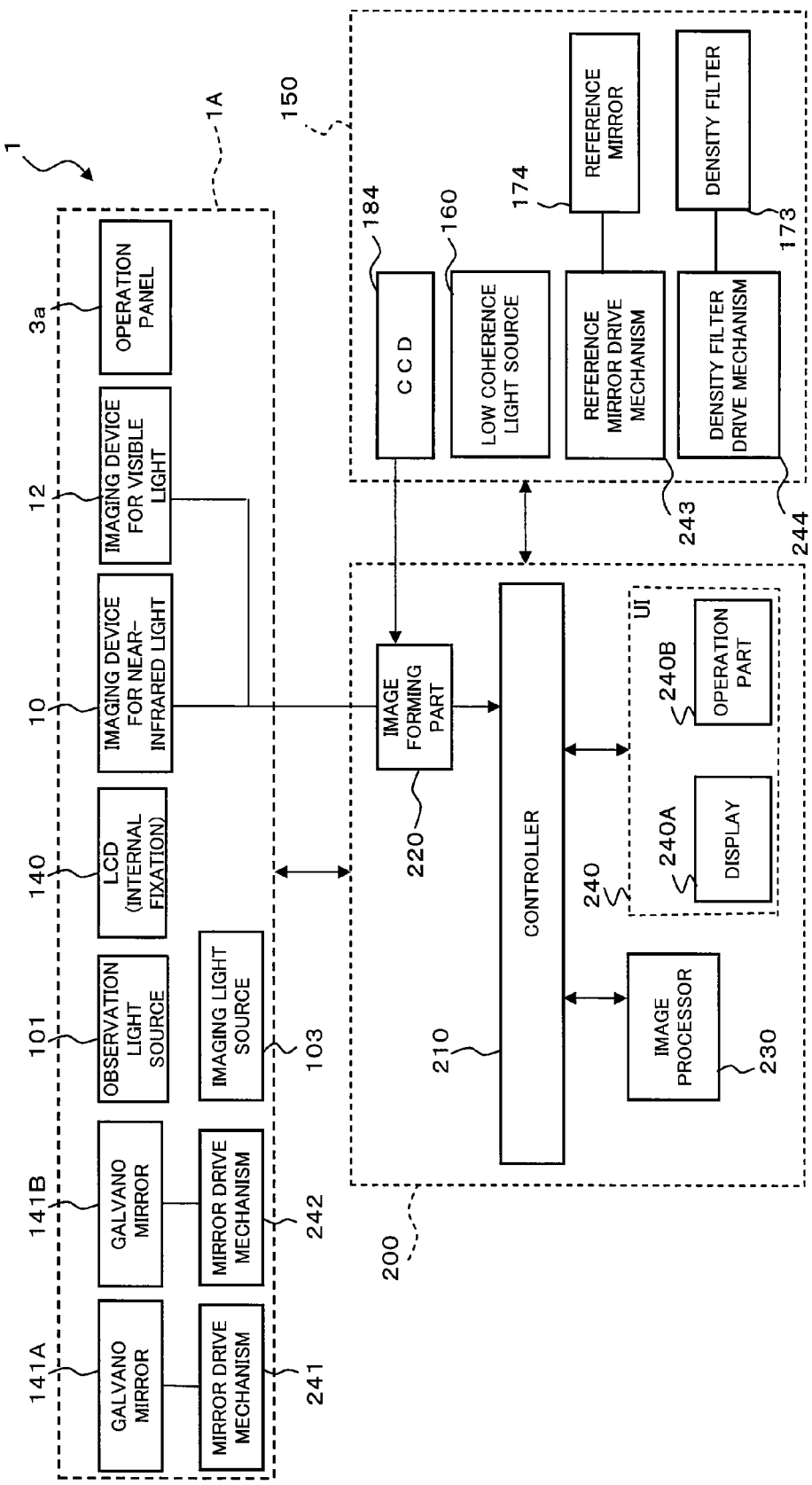
FIG. 5 is a schematic block diagram showing one example of the configuration of a control system in the preferred embodiment of the fundus oculi observation device according to the present invention.
Figure 6:
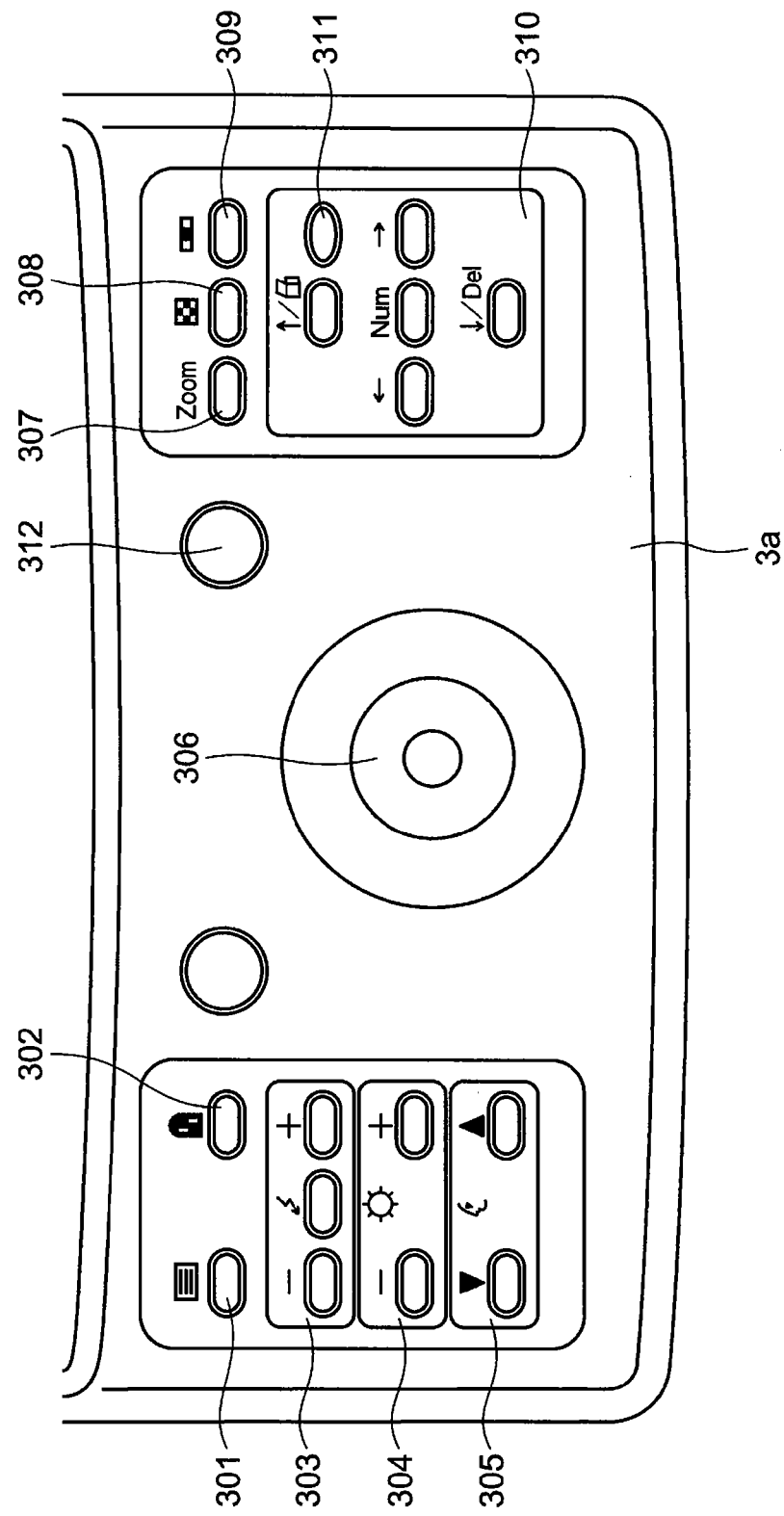
FIG. 6 is a schematic diagram showing an example of the appearance of an operation panel in the preferred embodiment of the fundus oculi observation device according to the present invention.
Figure 7:
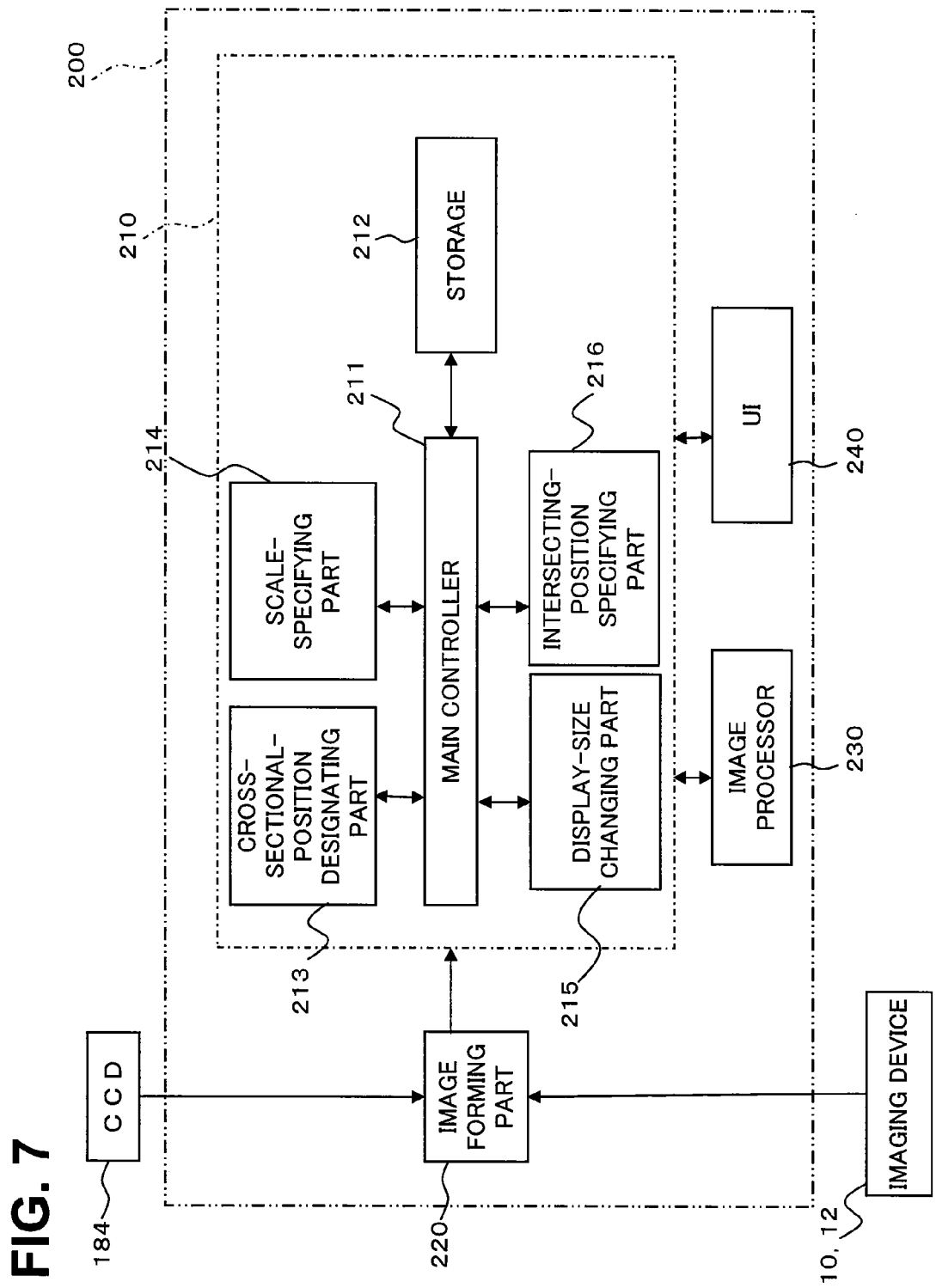
FIG. 7 is a schematic block diagram showing one example of the functional configuration of an arithmetic and control unit in the preferred embodiment of the fundus oculi observation device according to the present invention.

First, referring to FIGS. 1 through 7, the configuration of the fundus oculi observation device according to the present invention will be described. FIG. 1 shows one example of the entire configuration of a fundus oculi observation device 1 according to the present embodiment. FIG. 2 shows one example of the configuration of a scanning unit 141 in a retinal camera unit 1A. FIG. 3 shows one example of the configuration of an OCT unit 150. FIG. 4 shows a hardware configuration of an arithmetic and control unit 200. FIG. 5 shows one example of the configuration of a control system of the fundus oculi observation device 1. FIG. 6 shows one example of the configuration of an operation panel 3a disposed to the retinal camera unit 1A. FIG. 7 shows one example of the configuration of a control system of an arithmetic and control unit 200.

Entire Condiguration

Figure 16:
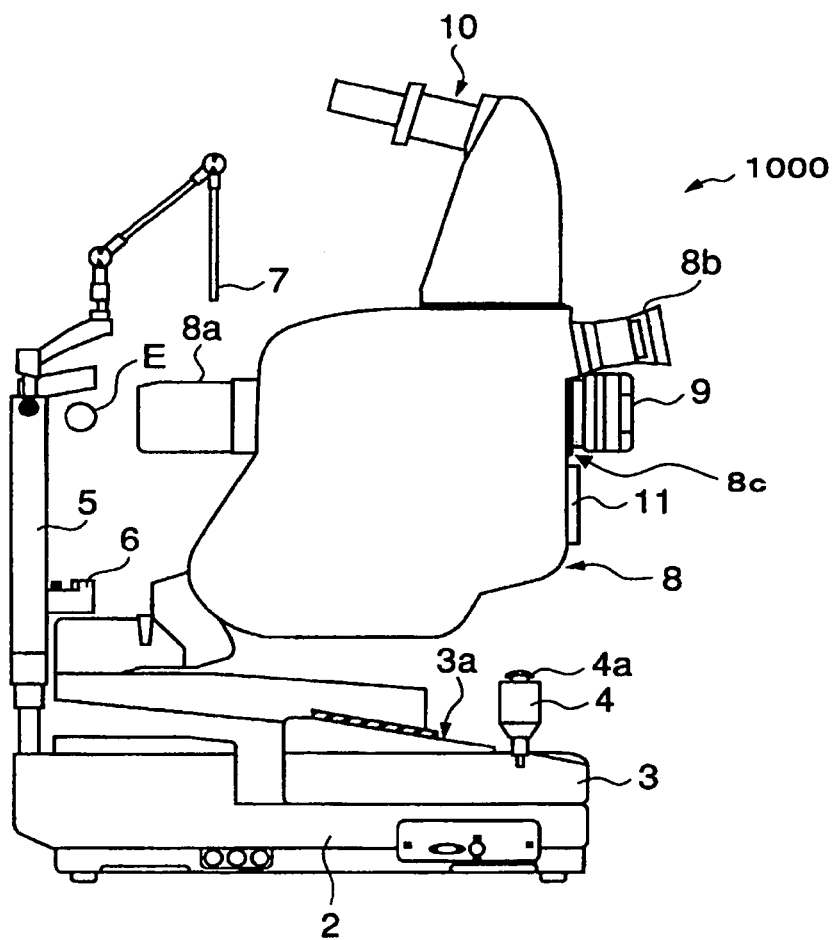
FIG. 16 is a schematic side view showing one example of the appearance of a conventional fundus oculi observation device (retinal camera)
Figure 17:
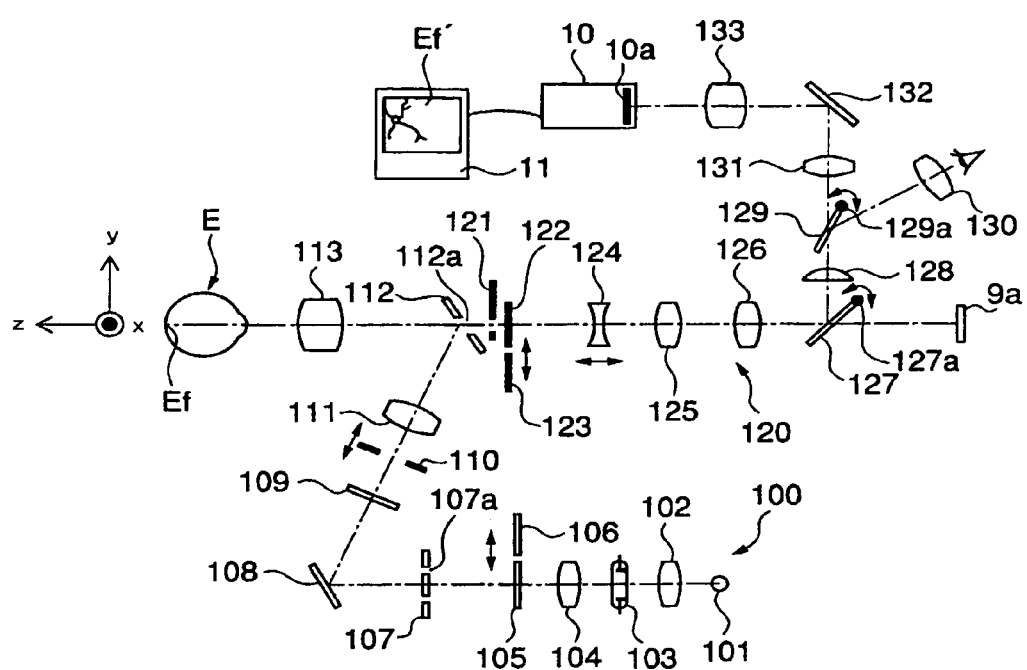
FIG. 17 is a schematic diagram showing one example of the internal configuration (optical system configuration) of a conventional fundus oculi observation device (retinal camera).

As shown in FIG. 1, the fundus oculi observation device 1 according to the present embodiment comprises: the retinal camera unit 1A that has the same function as a retinal camera of FIGS. 16 and 17; an OCT unit 150 accommodating an optical system of an optical image measurement device (OCT device); and the arithmetic and control unit 200 that executes various arithmetic processes, control processes, etc.

To the OCT unit 150, one end of a connection line 152 is attached. To the other end of the connection line 152, a connector part 151 is attached. The connector part 151 is mounted on a mounting part (refer to the mounting part 8c shown in FIG. 16) of a case of the retinal camera unit. Further, a conductive optical fiber runs through the inside of the connection line 152. Thus, the OCT unit 150 and the retinal camera unit 1A are optically connected via the connection line 152. The detailed configuration of the OCT unit 150 will be described later referring to FIG. 3.

Configuration of Retinal Camera Unit

The retinal camera unit 1A is a device configured to form an image of a fundus oculi Ef of an eye E, based on optically obtained data (data detected by imaging devices 10 and 12). The retinal camera unit 1A is particularly used to obtain an image of the surface of the fundus oculi of the eye E (such as a color 2D image and a fluorescein fluorescence image) or an image of the vicinity of the surface of the fundus oculi (an image of a shallow region of the fundus oculi surface such as an indocyanine green fluorescence image).

The retinal camera unit 1A has substantially the same appearance as the conventional retinal camera 5000 shown in FIG. 16. Further, as in the conventional optical system shown in FIG. 17, the retinal camera unit 1A is provided with an illumination optical system 100 that illuminates the fundus oculi Ef of the eye E, and an imaging optical system 120 that guides the fundus oculi reflection light of the illumination light to the imaging device 10.

Although the details will be described later, the imaging optical system 120 of the present embodiment is provided with the imaging device 10 for detecting the illumination light having a wavelength in the near-infrared region, and the imaging device 12 for detecting the illumination light having a wavelength in the visible region. In addition, the imaging optical system 120 acts so as to guide a signal light LS from the OCT unit 150 to the fundus oculi Ef, and guide the signal light LS passed through the fundus oculi Ef to the OCT unit 150.

As well as the conventional ones, the illumination optical system 100 comprises: an observation light source 101; a condenser lens 102; an imaging light source 103; a condenser lens 104; exciter filters 105 and 106; a ring transparent plate 107; a mirror 108; an LCD 109; an illumination diaphragm 110; a relay lens 111; an aperture mirror 112; and an objective lens 113.

The observation light source 101 emits an illumination light having a wavelength of the visible region included within, for example, about 400 nm to 700 nm. Further, the imaging light source 103 emits an illumination light having a wavelength in the near-infrared region included within, for example, about 700 nm to 800 nm. The near-infrared light emitted from this imaging light source 103 is set so as to have a shorter wavelength than the wavelength of the light used by the OCT unit 150 (described later).

The imaging optical system 120 comprises: an objective lens 113; an aperture mirror 112 (an aperture 112a thereof); an imaging diaphragm 121; barrier filters 122 and 123; a variable magnifying lens 124; a relay lens 125; an imaging lens 126; a dichroic mirror 134; a field lens 128; a half mirror 135; a relay lens 131; a dichroic mirror 136; an imaging lens 133; the imaging device 10 (image pick-up element 10a); a reflection mirror 137; an imaging lens 138; the imaging device 12 (image pick-up element 12a); a lens 139; and an LCD 140.

The imaging optical system 120 according to the present embodiment is different from the conventional imaging optical system 120 shown in FIG. 17 in that the dichroic mirror 134, the half mirror 135, the dichroic mirror 136, the reflection mirror 137, the imaging lens 138, the lens 139 and the LCD 140 are provided.

The dichroic mirror 134 reflects the fundus oculi reflection light (having a wavelength included within a range of about 400 nm to 800 nm) of the illumination light from the illumination optical system 100, and transmits a signal light LS (having a wavelength included within a range of, for example, about 800 nm to 900 nm; described later) from the OCT unit 150.

Further, the dichroic mirror 136 transmits the illumination light having a wavelength in the visible region from the illumination optical system 100 (visible light of a wavelength within about 400 nm to 700 nm emitted from the observation light source 101), and reflects the illumination light having a wavelength in the near-infrared region (near-infrared light of a wavelength within about 700 nm to 800 nm emitted from the imaging light source 103).

On the LCD 140, a fixation target (internal fixation target), etc. for fixing the eye E is displayed. The light from this LCD 140 is reflected by the half mirror 135 after being converged by the lens 139, and is reflected by the dichroic mirror 136 through the field lens 128. Then, the light passes through the imaging lens 126, the relay lens 125, the variable magnifying lens 124, the aperture mirror 112 (aperture 112a thereof), the objective lens 113, etc. and enters the eye E. As a result, an internal fixation target, etc. is projected in the fundus oculi Ef of the eye E.

The image pick-up element 10a is an image pick-up element such as a CCD and a CMOS installed in the imaging device 10 such as a TV camera, and is particularly used for detecting light having a wavelength of the near-infrared region (that is, the imaging device 10 is an infrared TV camera for detecting near-infrared light). The imaging device 10 outputs a video signal as a result of detection of near-infrared light.

A touch panel monitor 11 displays a 2-dimensional image (fundus oculi image Ef and the like) of the surface of the fundus oculi Ef, based on this video signal. This video signal is sent to the arithmetic and control unit 200, and the fundus oculi image Ef' and the like is displayed on the display (described later).

When the fundus oculi is imaged by the imaging device 10, for example, the illumination light emitted from the imaging light source 103 of the illumination optical system 100 and having a wavelength in the near-infrared region is used.

On the other hand, the image pick-up element 12a is an image pick-up element such as a CCD and a CMOS installed in the imaging device 12 such as a TV camera, and is particularly used for detecting light of a wavelength in the visible region (that is, the imaging device 12 is a TV camera for detecting visible light). The imaging device 12 outputs a video signal as a result of detection of visible light.

The touch panel monitor 11 displays a 2-dimensional image (fundus oculi image Ef and the like) of the surface of the fundus oculi Ef, based on this video signal. This video signal is sent to the arithmetic and control unit 200, and the fundus oculi image Ef' and the like is displayed on a display (described later).

At the time of fundus oculi imaging by the imaging device 12, for example, the illumination light emitted from the observation light source 101 of the illumination optical system 100 and having a wavelength in the visible region is used.

The imaging optical system 120 according to the present embodiment is provided with a scanning unit 141 and a lens 142. The scanning unit 141 comprises a configuration for scanning an application position of the signal light LS inputted by the OCT unit 150 to the fundus oculi Ef.

The lens 142 makes the signal light LS guided from the OCT unit 150 through the connection line 152 enter the scanning unit 141 in the form of a parallel light flux. Further, the lens 142 acts so as to converge the fundus oculi reflection light of the signal light LS passed through the scanning unit 141.

FIG. 2 shows one example of a specific configuration of the scanning unit 141. The scanning unit 141 comprises Galvano mirrors 141A, 141B, and reflection mirrors 141C, 141D.

The Galvano mirrors 141A and 141B are reflection mirrors disposed so as to be rotatable about rotary shafts 141a and 141b, respectively. The Galvano mirrors 141A and 141B are rotated about the rotary shafts 141a and 141b, respectively, by a drive mechanism described later (mirror drive mechanisms 241 and 242 shown in FIG. 5), whereby the orientations of reflection surfaces thereof (faces reflecting the signal light LS), namely, the positions of the Galvano mirrors 141A and 141B are changed, respectively.

The rotary shafts 141a and 141b are arranged perpendicular to each other. In FIG. 2, the rotary shaft 141a of the Galvano mirror 141A is arranged in parallel to the paper face of this figure, while the rotary shaft 141b of the Galvano mirror 141B is arranged perpendicular to the paper face of this figure.

That is, the Galvano mirror 141B is formed so as to be rotatable in the directions indicated by an arrow pointing in both directions in FIG. 2, while the Galvano mirror 141A is formed so as to be rotatable in the directions perpendicular to the arrow pointing in both the directions. As a result, this pair of Galvano mirrors 141A and 141B act so as to change the reflecting directions of the signal light LS to directions perpendicular to each other. As can be seen from FIG. 1 and FIG. 2, the signal light LS is scanned in the x direction when the Galvano mirror 141A is rotated, and the signal light LS is scanned in the y direction when the Galvano mirror 141B is rotated.

The signal lights LS reflected by the Galvano mirrors 141A and 141B are reflected by reflection mirrors 141C and 141D, thereby advancing in the same directions as having entered into the Galvano mirror 141A.

As described previously, the conductive optical fiber 152a runs inside the connection line 152, and an end face 152b of the optical fiber 152a is arranged facing the lens 142. The signal light LS emitted from this end face 152b advances while expanding its beam diameter toward the lens 142. The light is converged into a parallel light flux by this lens 142. On the contrary, the signal light LS passed through the fundus oculi Ef is converged toward the end face 152b by this lens 142, and guided to the optical fiber 152a.

Configuration of Oct Unit

Next, the configuration of the OCT unit 150 will be described referring to FIG. 3. The OCT unit 150 shown in FIG. 3 is a device configured to form a tomographic image of the fundus oculi based on optically obtained data (data detected by a CCD 184 described below).

The OCT unit 150 has a similar optical system to the conventional optical image measurement device. That is, the OCT unit 150 has: an interferometer that splits the light emitted from the light source into a reference light and a signal light and generates interference light by superposing the reference light passed through the reference object (reference mirror 174) and the signal light passed through an object to be measured (fundus oculi Ef); and a part configured to detect this interference light and output a detection signal as a result of the detection toward the arithmetic and control unit 200. The arithmetic and control unit 200 forms a tomographic image of the object to be measured, by analyzing this detection signal.

A low coherence light source 160 is composed of a broadband light source such as a super luminescent diode (SLD) and a light emitting diode (LED) that emits low coherence light L0. This low coherence light L0 is, for example, a light that has a wavelength in the near-infrared region and has a time-wise coherence length of approximately several tens of micrometers.

The low coherence light L0 has a longer wavelength than the illumination light (wavelength: about 400 nm to 800 nm) of the retinal camera unit 1A, for example, a wavelength included within about 800 nm to 900 nm.

The low coherence light L0 emitted from the low coherence light source 160 is guided to an optical coupler 162 through an optical fiber, 161 composed of, e.g. a single mode fiber or a PM (Polarization maintaining) fiber. The optical coupler 162 splits this low coherence light L0 into reference light LR and signal light LS.

The optical coupler 162 has both actions, i.e. a part (splitter) for splitting light, and a part (coupler) superposing lights); however, herein referred to as an "optical coupler" idiomatically.

The reference light LR generated by the optical coupler 162 is guided by an optical fiber 163 composed of a single mode fiber or the like, and emitted from the end face of the fiber. The emitted reference light LR is converged into a parallel light flux by a collimator lens 171, passed through a glass block 172 and a density filter 173, and then reflected by a reference mirror 174.

The reference light LR reflected by the reference mirror 174 is converged to the fiber end face of the optical fiber 163 by the collimator lens 171 again through the density filter 173 and the glass block 172. The converged reference light LR is guided to the optical coupler 162 through the optical fiber 163.

The glass block 172 and the density filter 173 act as a delaying part for matching the optical path lengths (optical distances) of the reference light LR and the signal light LS, and as a dispersion correction part for matching the dispersion characteristics of the reference light LR and the signal light LS.

In addition, the density filter 173 also acts as a dark filter for reducing the amount of the reference light, and is composed of a rotating ND (neutral density) filter, for example. This density filter 173 acts to change the reduction amount of the reference light LR by being rotary driven by a drive mechanism including a drive unit such as a motor (density filter drive mechanism 244 described later; refer to FIG. 5). That makes it possible to change the amount of the reference light LR contributing to generation of the interference light LC.

Furthermore, the reference mirror 174 is configured to be moved in the traveling direction (the direction of the arrow pointing both sides shown in FIG. 3) of the reference light LR. As a result, the light path length of the reference light LR according to the axial length of the eye E, etc. is ensured. The reference mirror 174 is moved by a drive mechanism (reference mirror driving mechanism 243 described later; refer to FIG. 5) including a driving part such as a motor.

Whereas, the signal light LS generated by the optical coupler 162 is guided to the end of the connection line 152 through an optical fiber 164 composed of a single mode fiber or the like. The conductive optical fiber 152a runs inside the connection line 152. Herein, the optical fiber 164 and the optical fiber 152a may be composed of a single optical fiber, or may be jointly formed by connecting the end faces of the respective fibers. In either case, it is sufficient as far as the optical fiber 164 and 152a are configured to be capable of transferring the signal light LS between the retinal camera unit 1A and the OCT unit 150.

The signal light LS is guided inside the connection line 152 and guided to the retinal camera unit 1A. Then, the signal light LS enters into the eye E through the lens 142, the scanning unit 141, the dichroic mirror 134, the imaging lens 126, the relay lens 125, the variable magnifying lens 124, the imaging diaphragm 121, the aperture 112a of the aperture mirror 112, and the objective lens 113. The barrier filter 122 and 123 are retracted from the optical path in advance, respectively, when the signal light LS is made to enter the eye E.

The signal light LS having entered the eye E forms an image on the fundus oculi (retina) Ef and is then reflected. At this moment, the signal light LS is not only reflected on the surface of the fundus oculi Ef, but also scattered at the refractive index boundary after reaching the deep area of the fundus oculi Ef. As a result, the signal light LS from the fundus oculi Ef is a light containing information reflecting the state of the surface of the fundus oculi Ef and the vicinity thereof and information reflecting the state of scatter in the rear at the refractive index boundary of the deep area tissue of the fundus oculi Ef. This light may be simply referred to as "fundus oculi reflection light of the signal light LS."

The fundus oculi reflection light of the signal light LS advances reversely on the above path within the retinal camera unit 1A to be converged at the end face 152b of the optical fiber 152a, enters into the OCT unit 150 through the optical fiber 152a, and returns to the optical coupler 162 through the optical fiber 164.

The optical coupler 162 overlays the signal light LS returning through the fundus oculi Ef on the reference light LR reflected at the reference mirror 174, thereby generating the interference light LC. The generated interference light LC is guided into a spectrometer 180 through an optical fiber 165 composed of a single mode fiber or the like.

Herein, the "interference optical generator" according to the present invention is composed of an interferometer including at least an optical coupler 162, optical fibers 163 and 164, and a reference mirror 174. Although a Michelson-type interferometer is adopted in the present embodiment, for instance, a Mach Zender type, etc. and any type of interferometer may be adopted appropriately.

The spectrometer 180 comprises a collimator lens 181, a diffraction grating 182, an image forming lens 183, and a CCD 184. The diffraction grating 182 in the present embodiment is a transmission-type diffraction grating that transmits light; however, needless to say, a reflection-type diffraction grating that reflects light may also be used. Furthermore, needless to say, it is also possible to adopt, in place of the CCD 184, other photo-detecting elements.

The interference light LC having entered the spectrometer 180 is split (resolved into spectra) by the diffraction grating 182 after converged into a parallel light flux by the collimator lens 181. The split interference light LC forms an image on the image pick-up surface of the CCD 184 by the image forming lens 183. The CCD 184 receives the interference light LC and converts to an electrical detection signal, and outputs the detection signal to the arithmetic and control unit 200.

Configuration of Aithmetic and Control Unit

Next, the configuration of the arithmetic and control unit 200 will be described. This arithmetic and control unit 200 corresponds to one example of each of the "fundus oculi image display device" and the "computer" according to the present invention.

The arithmetic and control unit 200 performs a process of analyzing the detection signal inputted from the CCD 184 of the spectrometer 180 of the OCT unit 150, and forming tomographic images of the fundus oculi Ef of the eye E. A technique for this analysis is the same technique as a conventional technique for the Fourier domain OCT.

Further, the arithmetic and control unit 200 performs a process of forming (image data of) images showing the state of the surface of the fundus oculi Ef and the vicinity thereof, such as two-dimensional images of the fundus oculi Ef (e.g., color images of the fundus oculi image Ef or the like), fluorescein fluorescence images and indocyanine green fluorescence images, based on the video signals outputted from the imaging devices 10 and 12 of the retinal camera unit 1A.

Furthermore, the arithmetic and control unit 200 executes control of each part of the retinal camera unit 1A and OCT unit 150.

The control of the retinal camera unit 1A is, for example: control of emission of illumination light by the observation light source 101 or the imaging light source 103; control of insertion/retraction operation of the exciter filters 105 and 106 or the barrier filters 122 and 123 to/from the optical path; control of the operation of a display device such as the LCD 140; control of shift of the illumination diaphragm 110 (control of the diaphragm value); control of the diaphragm value of the imaging diaphragm 121; and control of shift of the variable magnifying lens 124 (control of the magnification). Moreover, the arithmetic and control unit 200 executes control of the operation of the Galvano mirrors 141A and 141B inside the scanning unit 141 (operation of changing the directions of the reflection faces).

The control of the OCT unit 150 is, for example: control of emission of the low coherence light L0 by the low coherence light source 160; control of shift of the reference mirror 174; control of the rotary operation of the density filter 173 (operation of changing the reduction amount of the reference light LR); and control of the accumulated time of the CCD 184.

One example of the hardware configuration of the arithmetic and control unit 200 that acts as described above will be described referring to FIG. 4.

The arithmetic and control unit 200 is provided with a hardware configuration similar to that of a conventional computer. To be specific, the arithmetic and control unit 200 comprises: a microprocessor 201 (CPU, MPU, etc.), a RAM202, a ROM203, a hard disk drive (HDD) 204, a keyboard 205, a mouse 206, a display 207, an image forming board 208, and a communication interface (I/F) 209. These parts are connected via a bus 200a.

The microprocessor 201 executes operations characteristic to the present embodiment, by loading a control program 204a stored in the hard disk drive 204, onto the RAM 202. This control program 204a corresponds to one example of the "program" according to the present invention.

The microprocessor 201 executes control of each part of the device described above, various arithmetic processes, etc. Moreover, the microprocessor 201 executes control of each part of the device corresponding to an operation signal from the keyboard 205 or the mouse 206, control of a display process by the display 207, and control of a process of transmitting/receiving various data, control signals and so on by the communication interface 209.

The keyboard 205, the mouse 206 and the display 207 are used as user interfaces in the fundus oculi observation device 1. The keyboard 205 is used as, for example, a device for typing letters, figures, etc. The mouse 206 is used as a device for performing various input operations to the display screen of the display 207.

Further, the display 207 is an arbitrary display device composed of an LCD, a CRT (Cathode Ray Tube) display or the like. The display 207 displays various images of the fundus oculi Ef formed by the fundus oculi observation device 1, and displays various screens such as an operation screen and a set-up screen.

The user interface of the fundus oculi observation device 1 is not limited to the above configuration, and may be configured by using any user interface that is equipped with a function to display and output various information, and a function to input various information and operate the device, such as a track ball, a control lever, a touch panel type of LCD, and a control panel for ophthalmology examinations.

The image forming board 208 is a dedicated electronic circuit for a process of forming (image data of) images of the fundus oculi Ef of the eye E. This image forming board 208 is provided with a fundus oculi image forming board 208a and an OCT image forming board 208b.

The fundus oculi image forming board 208a is a dedicated electronic circuit that operates to form image data of fundus oculi images (color images, fluorescence images, or the like), based on the video signals from the imaging device 10 and the imaging device 12 of the retinal camera unit 1A.

Further, the OCT image forming board 208b is a dedicated electronic circuit that operates to form image data of tomographic images of the fundus oculi Ef, based on the detection signals from the CCD 184 of the spectrometer 180 in the OCT unit 150.

By providing the image forming board 208, it is possible to increase the processing speed for forming image data of fundus oculi images and tomographic images.

The communication interface 209 performs a process of sending the control signal from the microprocessor 201, to the retinal camera unit 1A or the OCT unit 150. Moreover, the communication interface 209 performs a process of receiving the video signals from the imaging devices 10 and 12 of the retinal camera unit 1A and the detection signal from the CCD 184 of the OCT unit 150, and inputting the signals to the image forming board 208. At this time, the communication interface 209 operates to input the video signals from the imaging devices 10 and 12, to the fundus oculi image forming board 208a, and input the detection signal from the CCD 184, to the OCT image forming board 208b.

In a case where the arithmetic and control unit 200 is connected to a network such as a LAN (Local Area Network) and the Internet, the communication interface 209 may be configured, equipped with a network adapter like a LAN card or communication equipment like a modem, so as to be able to perform data communication through the network. In this case, by installing a server accommodating the control program 204a on the network, and at the same time, configuring the arithmetic and control unit 200 as a client terminal of the server, it is possible to cause the fundus oculi observation device 1 to execute the operation according to the present invention.

Configuration of Control System

Next, the configuration of the control system of the fundus oculi observation device 1 will be described referring to FIG. 5 through FIG. 7. FIG. 5 is a block diagram showing a part related to the operations and processes according to the present invention particularly selected from among constituents composing the fundus oculi observation device 1. FIG. 6 shows one example of the configuration of the operation panel 3a disposed to the retinal camera unit 1A. FIG. 7 is a block diagram showing a detailed configuration of the arithmetic and control unit 200.

Controller

The control system of the fundus oculi observation device 1 is configured mainly having a controller 210 of the arithmetic and control unit 200 shown in FIG. 5. The controller 210 comprises the microprocessor 201, the RAM202, the ROM203, the hard disk drive 204 (control program 204a), and the communication interface 209.

The controller 210 executes the aforementioned controlling processes through the microprocessor 201 operating based on the control program 204a. In specific, for the retinal camera unit 1A, the controller 210 performs control of the mirror drive mechanisms 241 and 242 for changing the positions of the Galvano mirrors 141A and 141B, control of the display operation of the internal fixation target by the LCD 140, etc.

Further, for the OCT unit 150, the controller 210 performs control of the low coherence light source 160 and the CCD 184, control of the density filter drive mechanism 244 for rotating the density filter 173, control of the reference mirror drive mechanism 243 for moving the reference mirror 174 in the traveling direction of the reference light LR, etc.

Furthermore, the controller 210 performs control for causing the display 207 of the user interface (UI) 240 to display various images produced by the fundus oculi observation device 1: that is, images (color images, fluorescence images, etc.) of the surface of the fundus oculi Ef and the vicinity thereof obtained by the retinal camera unit 1A, and tomographic images of the fundus oculi Ef formed based on the detection signals obtained by the OCT unit 150. These images may be displayed on the display 207 separately, or may be displayed side by side simultaneously. The details of the configuration of the controller 210 will be described later referring to FIG. 7.

The controller 210 acting as described above functions as one example of the "controller" according to the present invention.

Image Forming Part

An image forming part 220 performs a process of forming image data of the fundus oculi image based on the video signals from the imaging devices 10 and 12 of the retinal camera unit 1A. Moreover, the image forming part 220 performs a process of forming image data of the tomographic images of the fundus oculi Ef based on the detection signals from the CCD 184 of the OCT unit 150. The imaging forming part 220 comprises the imaging forming board 208 and the communication interface 209. In this specification, "image" may be identified with "image data" corresponding thereto.

Image Processor

The image processor 230 applies various image processing to image data of images formed by the image forming part 220. For example, the image processor 230 executes a process of forming image data of a 3-dimensional image of the fundus oculi Ef based on the tomographic images corresponding to the detection signal from the OCT unit 150, and various correction processes such as brightness correction and dispersion correction of the images Herein, image data of a 3-dimensional image is image data made by assigning pixel values to each of a plurality of voxels arranged 3-dimensionally, and is referred to as volume data, voxel data, and the like. When displaying an image based on volume data, the image processor 230 operates to apply a rendering process (such as volume rendering and MIP (Maximum Intensity Projection)) to this volume data and form image data of a pseudo 3-dimensional image seen from a specified viewing direction. On a display device such as the display 207, the pseudo 3-dimensional image based on the image data is displayed.

The image processor 230 comprises the microprocessor 201, the RAM 202, the ROM 203, and the hard disk drive 204 (control program 204a).

A "first image forming part" according to the present invention comprises each part of the retinal camera unit 1A for capturing images of the surface of the fundus oculi Ef and the vicinity thereof, and the image forming part 220 (fundus oculi image forming board 208a). A "second image forming part" according to the present invention comprises each part of the retinal camera unit 1A for capturing tomographic images of the fundus oculi Ef, the OCT unit 150, the image forming part 220 (OCT image forming board 208b), and the image processor 230.

User Interface

The user interface (UI) 240 comprises a display 240A and an operation part 240B. The display 240A functions as one example of the "display" according to the present invention.

Further, the operation part 240B comprises an input device and an operation device such as the keyboard 205 and the mouse 206. The operation part 240B, which will be described in detail later, functions as one example of a "cross-sectional-pattern designating part" and a "cross-sectional-position designating part" according to the present invention.

Operation Panel

The operation panel 3a of the retinal camera unit 1A will be described below. As shown in FIG. 16, this operation panel 3a is arranged on the platform 3 of the retinal camera unit 1A, for example.

The operation panel 3a according to the present embodiment is, different from the conventional configuration described in Background of the Invention, provided with an operating part used to instruct an operation for capturing an image of the surface of the fundus oculi Ef and the vicinity thereof, and an operating part used to instruct an operation for capturing a tomographic image of the fundus oculi Ef (in the conventional configuration, only the former operating part is provided).

In the present embodiment, placement of the operation panel 3a makes it possible to execute an operation for capturing various images in the same manner as when operating a conventional retinal camera.

As shown in FIG. 6, the operation panel 3a is provided with, for example, a menu switch 301, a split switch 302, an imaging light amount switch 303, an observation light amount switch 304, a jaw holder switch 305, a photographing switch 306, a zoom switch 307, an image switching switch 308, a fixation target switching switch 309, a fixation target position adjusting switch 310, a fixation target size switching switch 311, and a mode switching knob 312.

The menu switch 301 is a switch operated to display a certain menu screen for a user to select and specify various menus (such as a photographing menu for photographing images of the surface of the fundus oculi Ef and the vicinity thereof and a tomographic image, and a setting menu for inputting various settings).

When this menu switch 301 is operated, the operation signal is inputted to the controller 210. The controller 210 causes the touch panel monitor 11 or the display 240A to display a menu screen, in response to the input of the operation signal. A controller (not shown) may be provided in the retinal camera unit 1A, whereby the controller causes the touch panel monitor 11 to display the menu screen.

The split switch 302 is a switch operated to switch the light on and off of the split bright line for focusing (e.g., see JP Patent laid-open No. H9-66031. Also referred to as split target, split mark and so on.). The configuration for projecting this split bright line onto the eye E (split bright line projection part) is housed, for example, in the retinal camera unit 1A (not shown in FIG. 1).

When this split switch 302 is operated, the operation signal is inputted to the controller 210 (or the aforementioned controller inside the retinal camera unit 1A; the same hereinafter). The controller 210 projects the split bright line onto the eye E by controlling the split bright line projection part, in response to the input of this operation signal.

The imaging light amount switch 303 is a switch operated to adjust the emitted light amount of the imaging light source 103 (photographing light amount) depending on the state of the eye E (such as the degree of opacity of the lens). This imaging light amount switch 303 is provided with, for example, a photographing light amount increasing switch "+" for increasing the photographing light amount, a photographing light amount decreasing switch "−" for decreasing the photographing light amount, and a reset switch (a button in the middle) for setting the photographing light amount to a predetermined initial value (default value).

When one of the imaging light amount switches 303 is operated, the operation signal is inputted to the controller 210. The controller 210 controls the imaging light source 103 in response to the inputted operation signal and adjusts the photographing light amount.

The observation light amount switch 304 is a switch operated to adjust the emitted light amount (observation light amount) of the observation light source 101. The observation light amount switch 304 is provided with, for example, an observation light amount increasing switch "+" for increasing the observation light amount, and an observation light amount decreasing switch "−" for decreasing the observation light amount.

When one of the observation light amount switches 304 is operated, the operation signal is inputted to the controller 210. The controller 210 controls the observation light source 101 in response to the inputted operation signal and adjusts the observation light amount.

The jaw holder switch 305 is a switch to move the position of the jaw holder 6 shown in FIG. 16. This jaw holder switch 305 is provided with, for example, an upward movement switch (upward triangle) for moving the jaw holder 6 upward, and a downward movement switch (downward triangle) for moving the jaw holder 6 downward.

When one of the jaw holder switches 305 is operated, the operation signal is inputted to the controller 210. The controller 210 controls a jaw holder movement mechanism (not shown) in response to the inputted operation signal and moves the jaw holder 6 upward or downward.

The photographing switch 306 is a switch used as a trigger switch for capturing a 2-dimensional image of the surface of the fundus oculi Ef and the vicinity thereof or a tomographic image of the fundus oculi Ef.

When the photographing switch 306 is operated in a state where a menu to photograph an image of the surface of the fundus oculi and the like is selected, the controller 210 that has received the operation signal controls the imaging light source 103 to emit photographing illumination light, and also causes the display 240A or the touch panel monitor 11 to display an image formed based on the video signal outputted from the imaging device 10 having detected the fundus oculi reflection light.

On the other hand, when the photographing switch 306 is operated in a state where a menu to capture a tomographic image is selected, the controller 210 that has received the operation signal controls the low coherence light source 160 to emit the low coherence light L0, and also controls the Galvano mirrors 141A and 141B to scan the signal light LS. Moreover, the controller 210 causes the display 240A or the touch panel monitor 11 to display a tomographic image of the fundus oculi Ef formed by the image forming part 220 (and image processor 230), based on the detection signal outputted from the CCD 184 that has detected the interference light LC.

The zoom switch 307 is a switch operated to change the angle of view (zoom magnification) at the time of photographing of the fundus oculi Ef. Every time this zoom switch 307 is operated, the photographing angle is set alternately to 45 degrees and 22.5 degrees, for example.

When this zoom switch 307 is operated, the controller 210 that has received the operation signal controls a variable magnifying lens driving mechanism (not shown) to move the variable magnifying lens 124 in the optical axis direction of the imaging optical system 120, thereby changing the photographing angle of view.

The image switching switch 308 is a switch operated to switch displayed images. A mode of switching the displayed images by the image switching switch 308 will be described later.

The fixation target switching switch 309 is a switch operated to switch the position of the internal fixation target displayed by the LCD 140 (i.e. the projection position of the internal fixation target on the fundus oculi Ef). By operating this fixation target switching switch 309, the display position of the internal fixation target can be switched, for example, among "fixation position to capture the image of the peripheral region of the center of the fundus oculi (fixation position for fundus oculi center imaging)," "fixation position to capture the image of the peripheral region of macula lutea (fixation position for macula lutea imaging)" and "fixation position to capture the image of the peripheral region of papilla (fixation position for papilla imaging)," in a circulative fashion.

In response to the operation signals from the fixation target switching switch 309, the controller 210 causes the LCD 140 to display the internal fixation target in different positions on the display surface thereof. The display positions of the internal fixation target corresponding to the above three fixation positions, for example, can be preset based on clinical data, or can be set for each eye E (image of the fundus oculi Ef) in advance.

The fixation target position adjusting switch 310 is a switch operated to adjust the display position of the internal fixation target. This fixation target position adjusting switch 310 is provided with, for example, an upward movement switch for moving the display position of the internal fixation target upward, a downward movement switch for moving it downward, a leftward movement switch for moving it leftward, a rightward movement switch for moving it rightward, and a reset switch for moving it to a predetermined initial position (default position).

Upon reception of the operation signal from either of these switches of the fixation target position adjusting switch 310, the controller 210 controls the LCD 140 to move the display position of the internal fixation target, in response to the operation signal.

The fixation target size switching switch 311 is a switch operated to change the size of the internal fixation target. When this fixation target size switching switch 311 is operated, the controller 210 that has received the operation signal controls the LCD 140 to change the display size of the internal fixation target. The display size of the internal fixation target can be switched, for example, between "normal size" and "enlarged size," alternately. As a result, the size of the projection image of the fixation target projected onto the fundus oculi Ef is changed. Upon reception of the operation signal from the fixation target position adjusting switch 311, the controller 210 controls the LCD 140 to change the display size of the internal fixation target, in response to the operation signal.

The mode switching knob 312 is a knob rotationally operated to selectively designate various photographing modes, such as a fundus oculi photographing mode to photograph a 2-dimensional image of the fundus oculi Ef, a fluorescence photographing mode to photograph a fluorescent image (a fluorescein fluorescence photographing mode, an indocyanine green fluorescence photographing mode), a B-scan mode to perform B-scan of the signal light LS, and a 3-dimensional scan mode to scan the signal light LS 3-dimensionally.

Herein, B-scan refers to scanning of the signal light LS for forming a tomographic image having a depth-wise (z-direction) cross section along a predetermined scanning line (for example, scanning line Ri shown in FIG. 8) (refer to, for example, NEDO Workshop "Seeing (examining) inside the body from the 'window' of the human body, the fundus oculi"—Development of an ultra early diagnostic device for lifestyle-related diseases using the latest optical technologies (held on Apr. 25, 2005), Internet, URL: http://www.nedo.go.jp/information/koubo/170627_2/besshi3.pdf).

In addition, this mode switching knob 312 may be configured so as to be capable of selecting a replay mode to replay and display a captured 2-dimensional image or tomographic image of the fundus oculi Ef. In addition, it may be configured so as to be capable of selecting a photographing mode to control so that the photographing of the fundus oculi Ef would be performed immediately after scanning of the signal light LS. Control of each part of the device for causing the fundus oculi observation device 1 to execute the operation corresponding to the each mode is executed by the controller 210.

Herein, the feature of control of scanning of the signal light LS by the controller 210, and the feature of processing to the detection signal from the OCT unit 150 by the image forming part 220 and the image processor 230 will be respectively described. An explanation regarding the process by the image forming part 220, etc., to the video signal from the retinal camera unit 1A will be omitted because it is the same as the conventional process.

Signal Light Scanning

Scanning of the signal light LS is performed by changing the positions (directions of the reflecting surfaces) of the Galvano mirrors 141A and 141B of the scanning unit 141 in the retinal camera unit 1A. By controlling the mirror drive mechanisms 241 and 242 respectively to change the directions of the reflecting surfaces of the Galvano mirrors 141A and 141B respectively, the controller 210 scans the application position of the signal light LS on the fundus oculi Ef.

When the facing direction of the reflecting surface of the Galvano mirror 141A is changed, the signal light LS is scanned in the horizontal direction (x-direction in FIG. 1) on the fundus oculi Ef. Whereas, when the facing direction of the reflecting surface of the Galvano mirror 141B is changed, the signal light LS is scanned in the vertical direction (y-direction in FIG. 1) on the fundus oculi Ef. Further, by changing the facing directions of the reflecting surfaces of both the Galvano mirrors 141A and 141B simultaneously, it is possible to scan the signal light LS in the composed direction of the x-direction and y-direction. That is, by controlling these two Galvano mirrors 141A and 141B, it is possible to scan the signal light LS in any direction on the x-y plane.

Figure 8A:
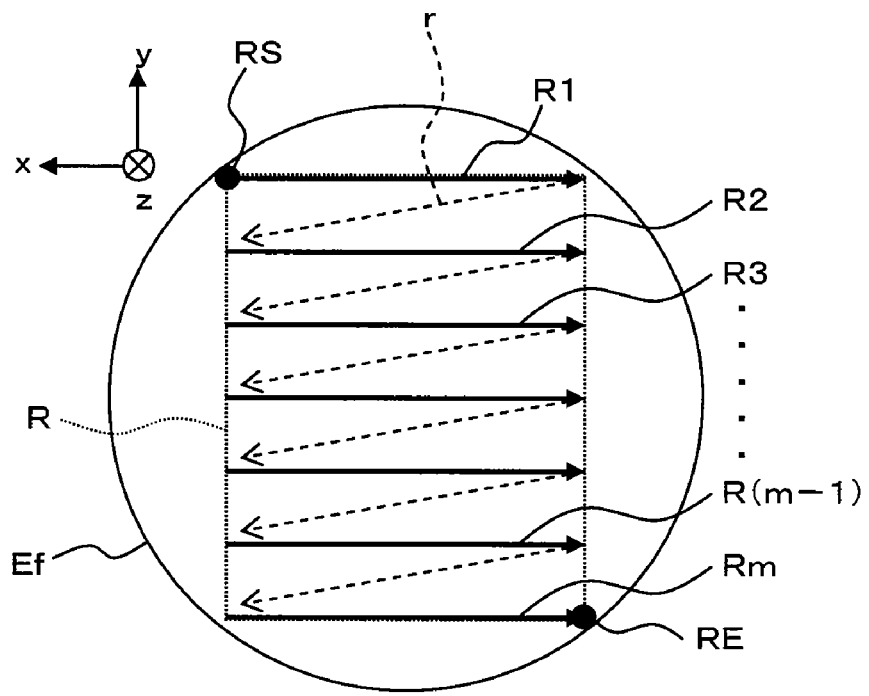
FIGS. 8A and 8B are schematic diagrams showing one example of the feature of scan of signal light in the preferred embodiment of the fundus oculi observation device according to the present invention.
Figure 8B:
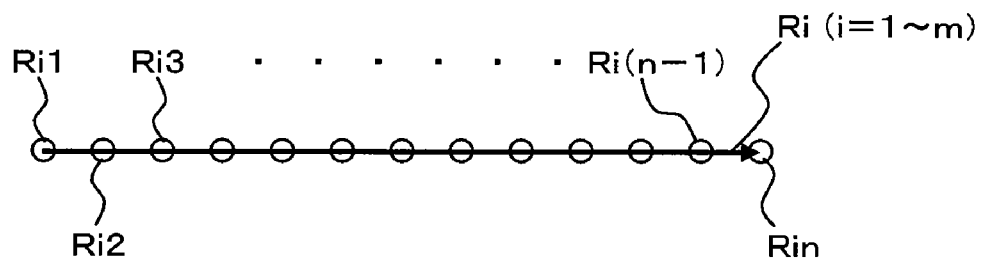

FIGS. 8A and 8B shows one example of the feature of scanning of the signal light LS for forming images of the fundus oculi Ef. FIG. 8A shows one example of the feature of scanning of the signal light LS, when the fundus oculi Ef is seen from a direction that the signal light LS enters the eye E (that is, seen from −z side toward +z side in FIG. 1). Further, FIG. 8B shows one example of the feature of arrangement of scanning points (positions at which image measurement is carried out; target positions of the signal light LS) on each scanning line on the fundus oculi Ef.

As shown in FIG. 8A, the signal light LS is scanned within a rectangular-shaped scanning region R that has been preset. Within this scanning region R, a plurality of (m number of) scanning lines R1 through Rm are set in the x-direction. When the signal light LS is scanned along the respective scanning lines Ri (i=1 through m), detection signals of the interference light LC are generated.

Herein, a direction of each scanning line Ri will be referred to as the "main scanning direction" and a direction orthogonal thereto will be referred to as the "sub-scanning direction". Accordingly, scanning of the signal light LS in the main scanning direction is performed by changing the facing direction of the reflecting surface of the Galvano mirror 141A, and scanning in the sub-scanning direction is performed by changing the facing direction of the reflecting surface of the Galvano mirror 141B.

On each scanning line Ri, as shown in FIG. 8B, a plurality of (n number of) scanning points Ri1 through Rin are preset.

In order to execute the scanning shown in FIGS. 8A and 8B, the controller 210 firstly controls the Galvano mirrors 141A and 141B to set the target of the signal light LS entering into the fundus oculi Ef to a scan start position RS (scanning point R11) on the first scanning line R1. Subsequently, the controller 210 controls the low coherence light source 160 to flush the low coherence light L0, thereby making the signal light LS enter the scan start position RS. The CCD 184 receives the interference light LC based on the fundus oculi reflection light of this signal light LS at the scan start position RS, and outputs the detection signal to the controller 210.

Next, the controller 210 controls the Galvano mirror 141A to scan the signal light LS in the main scanning direction and set the incident target of the signal light LS to a scanning point R12, and makes the low coherence light L0 flushed to make the signal light LS enter into the scanning point R12. The CCD 184 receives the interference light LC based on the fundus oculi reflection light of this signal light LS at the scanning point R12, and then outputs the detection signal to the controller 210.

Likewise, the controller 210 obtains detection signals outputted from the CCD 184 in response to the interference light LC for each scanning point, by flushing the low coherence light L0 at each scanning point while shifting the incident target of the signal light LS from scanning point R13 to R14, - - - , R1 (n−1), and R1n in order.

Once the measurement at the last scanning point R1n of the first scanning line. R1 is finished, the controller 210 controls the Galvano mirrors 141A and 141B simultaneously to shift the incident target of the signal light LS to the first scanning point R21 of the second scanning line R2 following a line switching scan r. Then, by conducting the previously described measurement on each scanning point R2j (j=1 through n) of this second scanning line R2, detection signals corresponding to the respective scanning points R2j are obtained.

Likewise, the measurement is conducted for each of the third scanning line R3, - - - , the m−1th scanning line R(m−1), the mth scanning line Rm to obtain the detection signals corresponding to the respective scanning points. Symbol RE on a scanning line Rm is a scan end position corresponding to a scanning point Rmn.

As a result, the controller 210 obtains m×n number of detection signals corresponding to m×n number of scanning points Rij (i=1 through m, j=1 through n) within the scanning region R. Hereinafter, a detection signal corresponding to the scanning point Rij may be represented by Dij.

Such interlocking control of the shift of scanning points and the emission of the low coherence light L0 can be realized by synchronizing, for instance, timing for transmission of control signals to the mirror drive mechanisms 241 and 242 and timing for transmission of control signals (output request signals) to the low coherence light source 160.

As described above, when each of the Galvano mirrors 141A and 141B is operated, the controller 210 stores the position of each scanning line Ri and the position of each scanning point Rij (coordinates on the x-y coordinate system) as information representing the content of the operation. This stored content (scanning point coordinate information) is used in an image forming process as in conventional one.

Image Processing

Next, one example of a process on OCT images (tomographiy images of the fundus oculi Ef) by the image forming part 220 and the image processor 230 will be described.

The image forming part 220 executes the formation process of tomographic images of the fundus oculi Ef along each scanning line Ri (main scanning direction). Further, the image processing section 230 executes the formation process of a 3-dimensional image of the fundus oculi Ef based on these tomographic images formed by the image forming part 220, the formation process of tomographic images of the three dimensional image. etc.

The formation process of a tomographic image by the image forming part 220, as in the conventionally one, includes a 2-step arithmetic process. In the first step of the arithmetic process, based on a detection signal Dij corresponding to each scanning point Rij, an image in the depth-wise direction (z-direction in FIG. 1) of the fundus oculi Ef at the scanning point Rij is formed.

Figure 9:
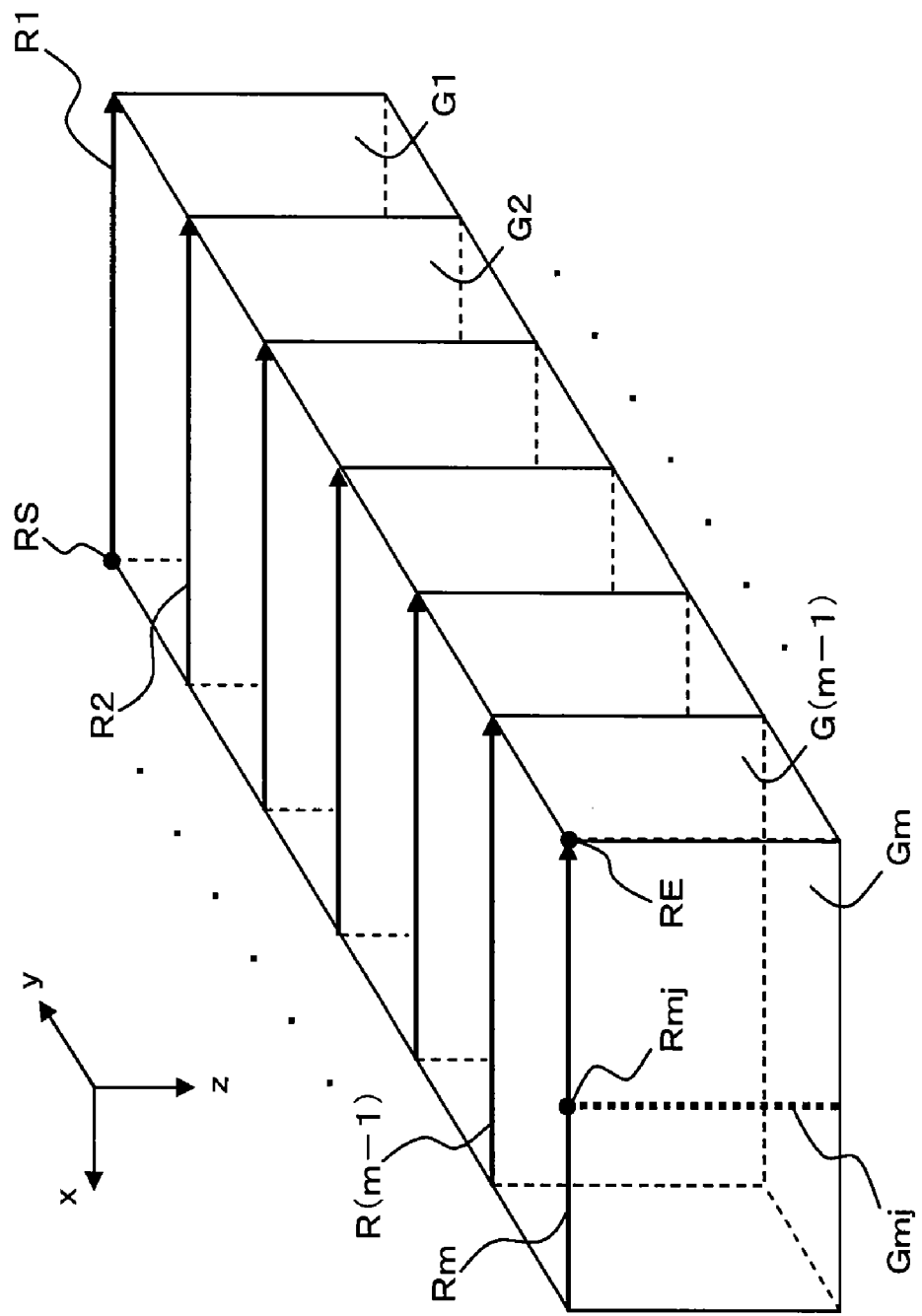
FIG. 9 is a schematic diagram showing one example of the feature of scan of signal light and the feature of a tomographic image formed along each scanning line in the preferred embodiment of the fundus oculi observation device according to the present invention.

FIG. 9 shows a feature of (a group of) tomographic images formed by the image forming part 220. In the second step of the arithmetic process, on each scanning line Ri, based on the images in the depth-wise direction at the n number of scanning points Ri1 through Rin, a tomographic image Gi of the fundus oculi Ef along the scanning line Ri is formed. Then, the image forming part 220 determines the arrangement and the distance of the scanning points Ri1 through Rin referring to the positional information (scanning point coordinate information described before) of the scanning points Ri1 through Rin, and forms a tomographic image Gi along this scanning line Ri.

Through the above process, m number of tomographic images (a group of tomographic images) G1 through Gm at different positions in the sub-scanning direction (y-direction) are obtained.

Next, the formation process of a 3-dimensional image of the fundus oculi Ef by the image processor 230 will be explained. A 3-dimensional image of the fundus oculi Ef is formed based on the m number of tomographic images obtained through the above arithmetic process. The image processor 230 forms a 3-dimensional image of the fundus oculi Ef by performing a known interpolating process to interpolate an image between the adjacent tomographic images Gi and G (i+1).

Then, the image processor 230 determines the arrangement and the distance of each scanning line Ri while referring to the positional information of each scanning line Ri to form this 3-dimensional image. For this 3-dimensional image, a 3-dimensional coordinate system (x, y, z) is set, based on the positional information (the scanning point coordinate information) of each scanning point Rij and the z-coordinate in the depth-wise image.

Furthermore, based on this 3-dimensional image, the image processor 230 can form a tomographic image of the fundus oculi Ef at a cross-section in any direction other than the main scanning direction (x-direction). Once the cross-section is designated, the image processor 230 determines the position of each scanning point (and/or an interpolated depth-wise image) on this designated cross-section, and extracts a depth-wise image at each determined position (and/or an interpolated depth-wise image), thereby foring a tomographic image of the fundus oculi Ef at the designated cross-section by arranging plural extracted depth-wise images.

Furthermore, an image Gmj shown in FIG. 9 represents an image in the depth-wise direction (z-direction) at the scanning point Rmj on the scanning line Rm. A depth-wise image at each scanning point Rij on the scanning line Ri formed by the first-step arithmetic process is represented as "image Gij."

Detailed Configuration of Arithmetic and Control Unit

A detailed configuration of the arithmetic and control unit 200 will be described referring to FIG. 7. Herein, the controller 210 will be detailed specifically.

The controller 210 is provided with a main controller 211, a storage 212, the cross-sectional-position designating part 213, a scale-specifying part 214, a display-size changing part 215, and the intersecting-position specifying part 216.

Main Controller

The main controller 211 executes the abovementioned various control processes by the controller 210, such as display control of an image or a screen by the display 240A. In addition, the main controller 211 performs a process for storing images (image data) or various types of information on the storage 212 and a process for reading the images and the various types of information from the storage 212. Moreover, the main controller 211 controls the cross-sectional-position designating part 213, the scale-specifying part 214, the display-size changing part 215, and the intersecting-position a specifying part 216 in order to execute a process to be described later.

Storage

The storage 212 stores (image data of) images that have been formed by the image forming part 220 or the image processor 230, various types of information regarding the images, etc. The various information that can be stored may, for example, include patient information such as the name and age of a patient, imaging information that includes imaging conditions such as the imaging date and time, the imaging magnification ratio, and the imaging light amount related to a color image or a fluorescence image, imaging information that includes imaging conditions such as the imaging date and time and the scanning point coordinate information related to a tomographic image, etc.

The storage 212 functions as one example of the "storage" in the "fundus oculi image display device" or the "computer" according to the present invention, and is configured to include, for example, a relatively high-capacity storage device such as a hard disk drive 204.

Cross-sectional-position Designating Part

The cross-sectional-position designating part 213 performs, for a fluorescence image and a tomographic image displayed on the display 240A, a process for specifying the cross-sectional position of the tomographic image on the fluorescence image. In addition, the cross-sectional-position designating part 213 performs, for a color image and a tomographic image displayed on the display 240A, a process for specifying the cross-sectional position of the tomographic image on the color image. One example of these processes will be explained below.

On the display 240A, A coordinate system ($\xi$, $\eta$) representing the position thereof on the display screen is set in advance.

The coordinate system (ξ, η) that can be applied may include, for example, a 2D coordinate system that represents the position of each pixel on the screen of the display 207 or the like.

The coordinate system (ξ, η) are employed as image position information that represents the position on a fluorescence image or a color image on the display screen. In addition, the coordinate system (ξ, η) are associated with the abovementioned scanning point coordinate information (x, y) in advance. This association can be performed, for example, based on the imaging magnification ratio, the displaying magnification ratio, etc.

Therefore, the position on the displayed fluorescence image or color image and the position at a 3D coordinates (x, y, z) that is set for a tomographic image of an arbitrary cross section or a 3D image based on tomographic images G1 through Gm or at a partial coordinate system thereof (such as (x, z) and (y, z)) will be associated with each other.

The cross-sectional-position designating part 213 specifies the cross-sectional position of the tomographic image on the fluorescence image or the color image by referencing this association. Incidentally, as will be described in detail below, the controller 210 displays cross-sectional-position information of the fluorescence image or the color image, based on the result specified by the cross-sectional-position designating part 213.

Scale-specifying Part

The scale-specifying part 214 performs a process for specifying a predetermined distance on a fluorescence image, color image, or tomographic image that is displayed on the display 240A. This predetermined distance may, for example, include a distance of approximately 1 mm to a few mm that is set in advance.

The pixel space on a display screen corresponds to a distance, depending on the imaging magnification ratio or the displayed magnification ratio (distance in a real space). The scale-specifying part 214 specifies a predetermined distance on the image, based on this correspondence relationship, as well as the imaging magnification ratio and the displaying magnification ratio of the image, etc. This predetermined distance may be a constant value, or may vary depending on the imaging magnification ratio, the displaying magnification ratio, etc.

Incidentally, as will be described in detail later, the controller 210 displays, based on the result specified by the scale-specifying part 214, a scale image that represents a predetermined distance overlapping a fluorescence image or the like. This scale image is composed of, for example, a linear image representing the abovementioned predetermined distance in the x direction, a linear image representing the abovementioned predetermined distance in the y direction, or an image that is a combination thereof.

Display-size Changing Part

When both a fluorescence image and a color image are displayed, the display-size changing part 215 performs a process for adjusting the display size of these images to each other. More specifically, the display-size changing part 215 matches the display size of the fluorescence image and the color image, based on the imaging magnification ratio or the like of the fluorescence image and the color image.

Alternatively, the display-size changing part 215 may also be configured to change the display size for two or more feature points of the fundus oculi Ef by comparing the position of feature points on a fluorescence image and the position of the feature points on a color image so as to match the positions of the feature points on these images with each other. Thus, the consideration of feature points enables position adjustment between the color image and the fluorescence image.

Herein, display size refers to the size of an object to be imaged (fundus oculi Ef) on a display image. Therefore, for a distance between predetermined positions in a display image (such as the distance between the center position of optic papilla and the fovea centralis or the thickness of a certain blood vessel), the distance in the fluorescence image and the distance in the color image will be matched with each other by adjusting the display size to each other. The display-size changing part 215 is equivalent to an example of the "display size-changing part" of the present invention.

In addition, the display-size changing part 215 acts so as to match the display size of a color image or a fluorescence image with the display size of a tomographic image.

For that purpose, the display-size changing part 215 forms an image (accumulated image) in which the respective tomographic images Gi (image Gij in the depth direction) are accumulated in the depth direction (z direction) of the fundus oculi Ef, for example, when m number of tomographic images G1 through Gm have been obtained. Herein, "accumulating in the depth direction" means an arithmetic processing for adding up (or projecting) in the depth direction, the brightness values of the respective positions in the depth direction of the images Gij in the depth direction. Incidentally, the accumulated image is described in detail in, for example, Japanese Patent Application 2005-337628 filed by the present applicant.

The accumulated image obtained in this way is an image that represents morphology of the surface of a fundus oculi, as in the case with the color image or the fluorescein fluorescence image. However, the accumulated image is formed in only the scanning region R. The display-size changing part 215 can match the display sizes of a color image or the like and a tomographic image (3D image) with each other by matching the display size of a partial image in the scanning region R of the color image (or fluorescein fluorescence image or the like) and the display size of an accumulated image. Incidentally, the display size in the z direction of the tomographic image or the 3D image can be changed in accordance with the change in display size in the x-y direction.

In addition, the display-size changing part 215 can also perform alignment of the partial image in the scanning region R of the color image or the like and the accumulated image. This process can be executed, for example, by applying the known pattern-matching process or the like. By performing such alignment, it is possible to align the color image or the like and the tomographic image.

Furthermore, the display-size changing part 215 can also match the display size or position of an image that represents the vicinity (shallow region) of the surface of the fundus oculi, such as an indocyanine green fluorescence image, with the display size or position of a tomographic image.

For that purpose, the display-size changing part 215, for example, compares the morphology of an x-y tomographic image (tomographic image at a constant depth z) based on a 3D image formed from a tomographic image, with the morphology of an indocyanine green fluorescence image, thereby specifying an x-y tomographic image with a depth of $z=z0$ in which the morphologies are (almost) matched. This x-y tomographic image is formed in only the scanning region R. The display-size changing part 215 can match the display sizes or align the positions of the indocyanine green fluorescence image and the tomographic image as is the case such as with the color image, by taking this x-y tomographic image into account.

Intersecting-position Specifying Part

In the case of display of two or more tomographic images for which the cross-sectional positions are different from each other, the intersecting-position specifying part 216 specifies the intersecting position of these cross-sectional positions. This process will be explained more specifically hereinafter. First, the intersecting-position specifying part 216 specifies, for each of the two or more tomographic images, the cross-sectional position thereof by the abovementioned coordinate system (x, y, z), for example. Next, the intersecting-position specifying part 216 determines, based on the specified cross-sectional position of each of the tomographic images, whether an intersecting cross-sectional position exists. When the intersecting cross-sectional position exists, the intersecting-position specifying part 216 specifies the intersecting position, based on the abovementioned coordinate system.

Herein, the intersecting-position specifying part 216 may also specify the cross-sectional position of each tomographic image by employing the coordinate system (x, y) on a fluorescence image or a color image, and determine whether an intersecting cross-sectional position exists.

First Aspect of Usage

Figure 10:
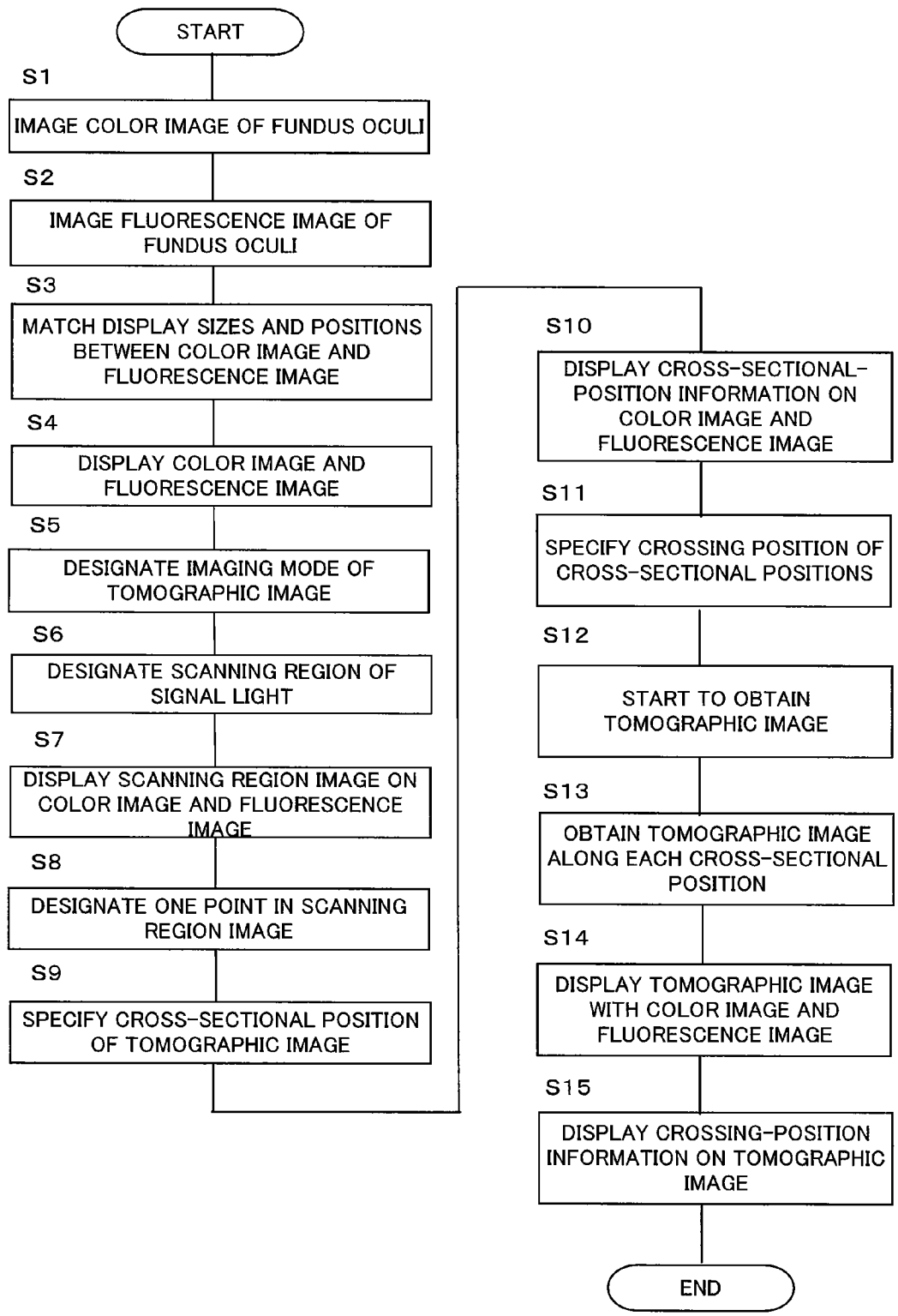
FIG. 10 is a flowchart showing one example of the usage mode of the preferred embodiment of the fundus oculi observation device according to the present invention.

Aspects of using the fundus oculi observation device 1 having the configuration as described above will be explained hereunder. FIG. 10 shows an example of aspects of using the fundus oculi observation device 1.

First, a color image of the surface of the fundus oculi Ef is imaged (S1) and a fluorescence image of the fundus oculi Ef is imaged (S2), by using the fundus oculi observation device 1. The image data of the obtained color image and fluorescence image are stored in the storage 212 of the arithmetic and control unit 200 along with each imaging information or the like.

Incidentally, the order of imaging a color image and a fluorescence image is discretionary. In addition, imaging of the color image and imaging of the fluorescence image does not need to be done successively but may be done at a different date and time. In this aspect of usage, it is sufficient if both a color image and a fluorescence image of the fundus oculi Ef are obtained.

Imaging of a color image is performed in a state in which the exciter filters 105 and 106 of the retinal camera unit 1A are retracted from the light path of the illumination optical system 100 and in which the barrier filters 122 and 123 are retracted from the light path of the imaging optical system 120, as is the case with a normal retinal camera.

Meanwhile, the imaging of a fluorescence image is performed in a state in which the exciter filter 105 (or exciter filter 106) is placed on the light path of the illumination optical system 100 and in which the barrier filter 122 (or barrier filter 123) is placed on the light path of the imaging optical system 120, along with administering (e.g., intravenously) a fluorescent agent to a subject in advance, as is the case with a normal retinal camera.

In addition, in the imaging of a fluorescence image, a fluorescein fluorescence image that represents the condition of blood vessels on the surface of the fundus oculi Ef may be imaged only, an indocyanine green fluorescence image that represents the condition of blood vessels in the vicinity of the surface (shallow region) of the fundus oculi Ef may be imaged only, or both fluorescence images may be imaged. Hereunder, is assumed that both fluorescence images have been will be imaged.

Incidentally, the filters can be inserted/removed into/from the light path by switching the imaging modes, for example, by operating the mode-switching knob 312.

The display-size changing part 215 matches the display sizes of the color image obtained in Step S1 and the fluorescence image obtained in Step S2 (the fluorescein fluorescence image and the indocyanine green fluorescence image) and matches the positions thereof with each other (S3). The main controller 211 displays, side-by-side on the display 240A, the color image and the fluorescence images for which display size and position have been adjusted (S4).

Figure 11:
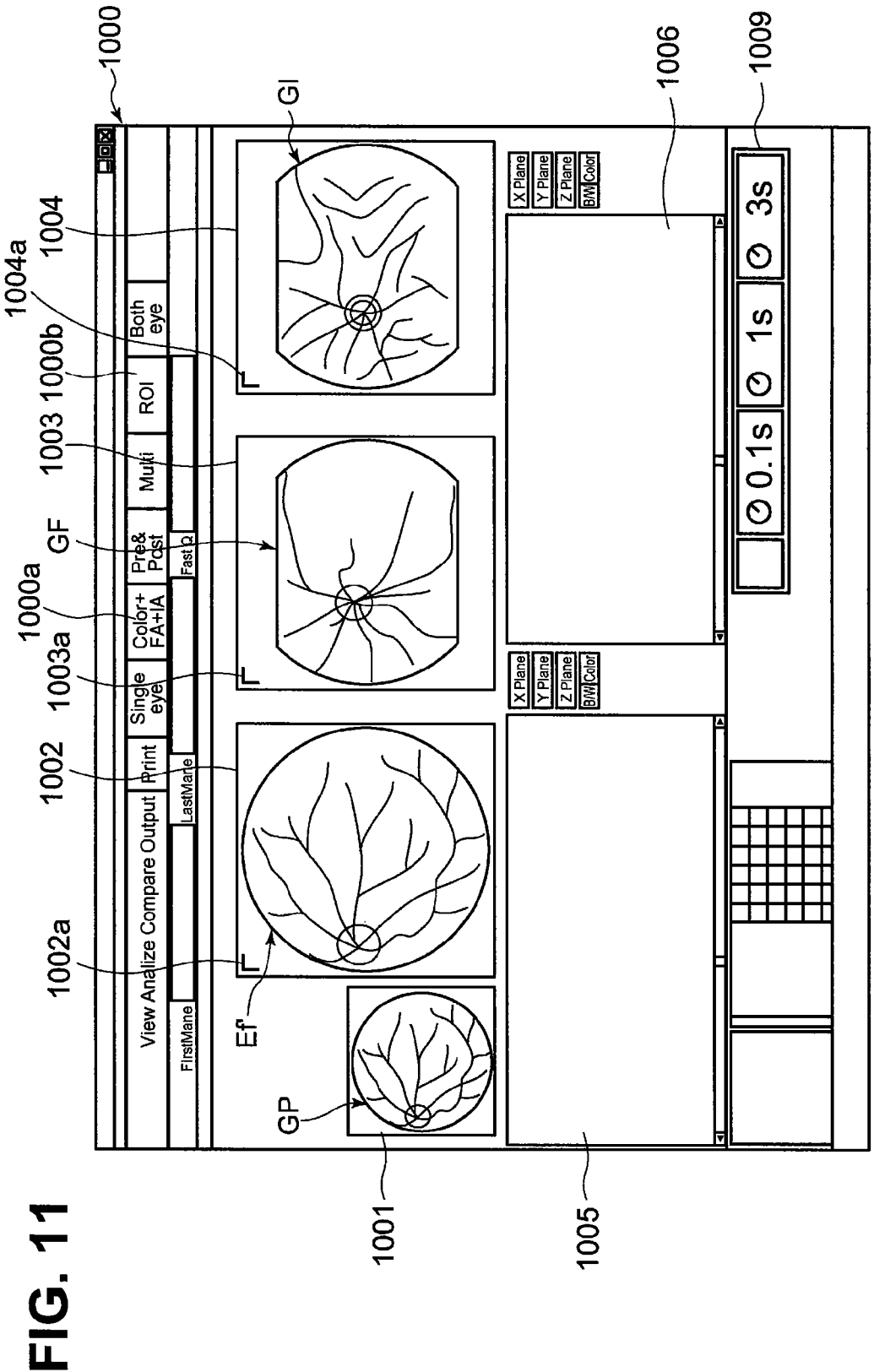
FIG. 11 is a schematic diagram showing one example of a display screen displayed in a preferred embodiment of the fundus oculi observation device according to the present invention.

FIG. 11 shows an example of a display screen that presents various fundus oculi images. A display mode designation button for selectively designating various display modes is situated on the upper portion of a fundus oculi observation display 1000 shown in the figure.

This display mode designation button is specifically provided with a first designation button 1000a for displaying a color image, fluorescein fluorescence image and indocyanine green fluorescence image of the fundus oculi Ef side by side, and a second designation button 1000b for displaying a tomographic image in a region of interest (ROI) in various morphologies along with the color image or fluorescence image. FIG. 11 shows morphology of the fundus oculi observation display 1000 when the first designation button 1000a is operated (clicked).

The fundus oculi observation display 1000 shown in FIG. 11 is provided with an observation position image display part 1001, a color image display part 1002, a fluorescein fluorescence image display part 1003, an indocyanine green fluorescence image display part 1004, and tomographic image display parts 1005 and 1006. In addition, this fundus oculi observation display 1000 is provided with a tomographic image imaging mode specifying part 1009.

The observation position image display part 1001 displays an image that indicates the observation position of the fundus oculi Ef (observation position image GP). The observation position image GP is, for example, a color image of the fundus oculi Ef (displayed on the color image display part 1002).

The color image display part 1002 displays the color image Ef' of the fundus oculi Ef (fundus oculi image) obtained in Step S1. In addition, the fluorescein fluorescence image display part 1003 displays a fluorescein fluorescence image GF of the fundus oculi Ef obtained in Step S2. Moreover, the indocyanine green fluorescence image display part 1004 displays an indocyanine green fluorescence image GI of the fundus oculi Ef also obtained in Step S2.

Incidentally, as shown in FIG. 11, the color image display part 1002, the fluorescein fluorescence image display part 1003, and the indocyanine green fluorescence image display part 1004 displays, respectively, scale images 1002a, 1003a, and 1004a, according to the display sizes of the color image Ef', the fluorescein fluorescence image GF, and the indocyanine green fluorescence image GI. The main controller 211 controls so as to display these scale images 1002a, 1003a, and 1004a, based on the predetermined distance in the image that has been specified by the scale-specifying part 214. Incidentally, in this aspect of usage, the display size is adjusted for the images Ef', GF, and GI (Step S3), so that each of the scale images 1002a, 1003a, and 1004a will be displayed in the same size.

Further, a tomographic image of the fundus oculi Ef is displayed in the tomographic image display parts 1005 and 1006, but the tomographic image is not displayed yet in the state shown in FIG. 11 (the phase before the cross-sectional position is designated).

The tomographic image imaging mode specifying part 1009 is for designating various imaging modes of a tomographic image of the fundus oculi Ef. The tomographic image imaging mode specifying part 1009 is provided with, for example, a 0.1s button for specifying a 0.1-sec imaging mode, a 1s button for specifying a 1-sec imaging mode, and a 3s button for specifying a 3-sec imaging mode. The examiner can specify a desired imaging mode by clicking a button corresponding to the imaging mode.

The 0.1-sec imaging mode is an imaging mode for obtaining, for example, a B-scan image of two cruciform cross-sectional positions (e.g., the lateral resolution is 1024 ppi). This 0.1-sec imaging mode has the merit that the measurement time is short (approximately 0.1 seconds) and the lateral resolution is high, but has the demerit that 3D images cannot be formed and the accuracy of alignment of images is relatively low.

The 1-sec imaging mode is an imaging mode for obtaining, for example, 32 sheets of the lateral B-scan images (e.g., the lateral resolution is 256 ppi). Consequently, the B-scan images (tomographic images) GI through G32 (cf. FIG. 9) are obtained. With this 1-sec imaging mode, a 3D image can be formed within a relatively short measurement time (approximately 1 second), but the number of sheets obtained is small, and therefore, only a 3D image with relatively low resolution can be obtained.

The 3-sec imaging mode is an imaging mode for obtaining 256 lateral B-scan images (e.g., the lateral resolution is 256 ppi). Consequently, the B-scan images (tomographic images) GI through G256 (cf. FIG. 9) are obtained. This 3-sec imaging mode takes a relatively long measurement time (approximately 3 seconds), but a high-definition 3D image can be formed, because the interval between adjacent tomographic images Gi and G (i+1) is narrow, and the position of images can be adjusted with relatively high accuracy.

These imaging modes are selected and applied as necessary, in accordance with the type of accident or sickness, the condition of the affected area, the diagnostic method, etc. Hereinafter, the imaging aspect of the tomographic image of the fundus oculi Ef is explained.

The examiner operates the operation part 240B (the mouse 206, or the like) to specify an imaging mode of a tomographic image (S5). Herein, it is assumed that the 0.1-sec imaging mode is specified in Step S5.

Figure 12:
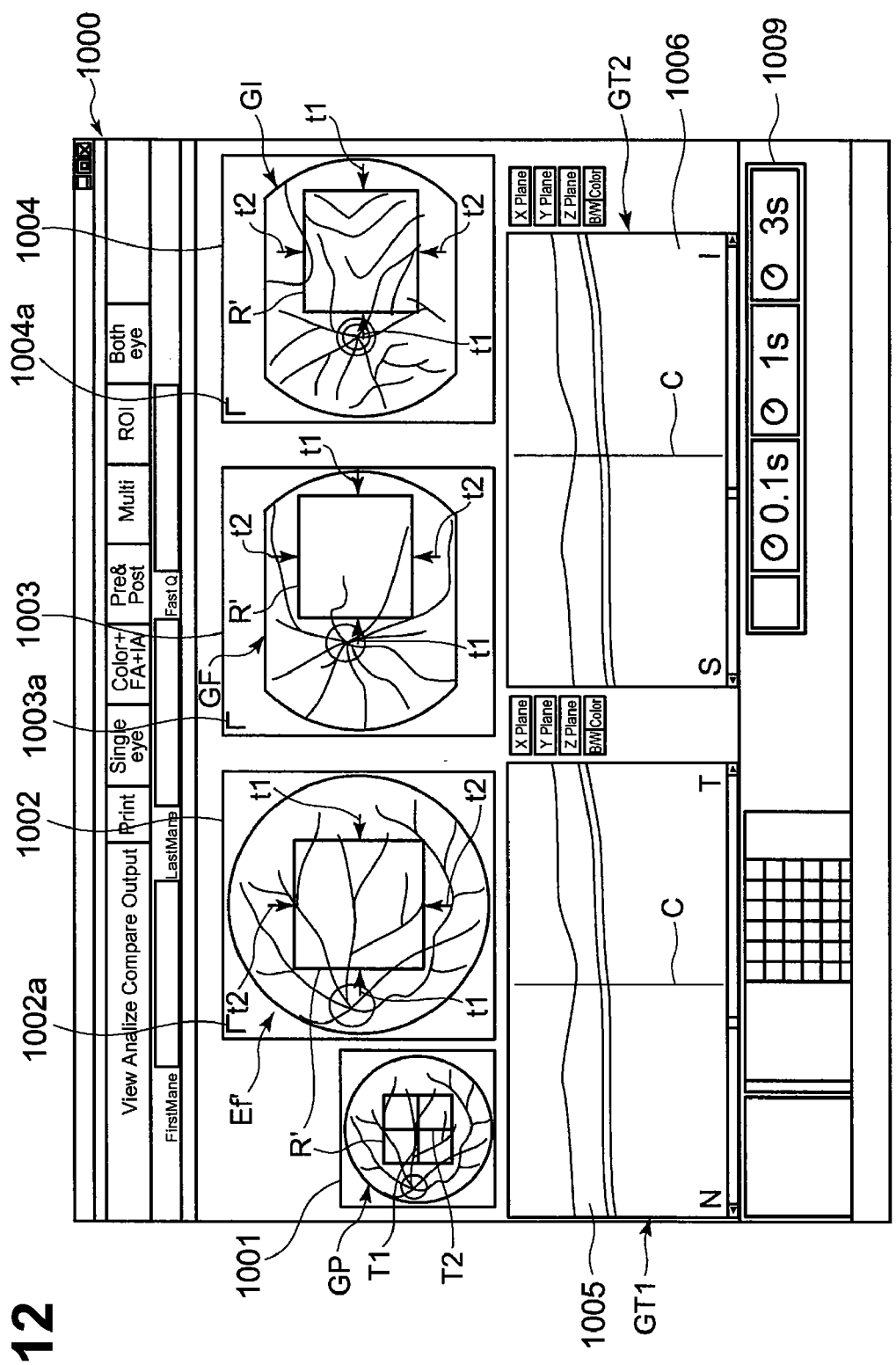
FIG. 12 is a schematic diagram showing one example of a display screen displayed in a preferred embodiment of the fundus oculi observation device according to the present invention.

Further, the examiner operates the operation part 240B to designate the scanning region R (e.g., 6 mm×6 mm) shown in FIG. 8A (S6). The main controller 211 displays a scanning region image R' indicating an image region equivalent to the designated scanning region R, so as to overlap the color image Ef', the fluorescein fluorescence image GF, and the indocyanine green fluorescence image GI, as shown in FIG. 12 (S7).

Furthermore, the examiner designates a single point in the scanning region image R' on the color image Ef' (or the fluorescence image GF or GI) (S8). This designation operation is performed, for example, by clicking a desired single point in the scanning region image R' with a mouse 206.

The cross-sectional-position designating part 213 specifies, based on morphology of the cross section (scanning line of the signal light LS) indicated in the imaging mode designated in Step S5 and the position of the single point designated in Step S8, the cross-sectional positions of each of the color image Ef' and the fluorescence images GF and GI (S9).

In this explanation, the 0.1-sec imaging mode is designated as described above. The cross-sectional-position designating part 213 specifies two cross-sectional positions that intersect each other at a single point designated in Step S8. Incidentally, the position has been adjusted in Step S3 between the color image Ef' and the fluorescence images GF and GI, so it is possible to easily specify the cross-sectional position of another image by specifying the cross-sectional position in one of these images.

The main controller 211 displays information that represents the cross-sectional position specified in Step S9 (cross-sectional-position information) so as to overlap each of the color image Ef' and the fluorescence images GF and GI (S10). In addition, the cross-sectional-position information is displayed also on the observation position image GP. One example of the display form of the cross-sectional-position information is shown in FIG. 12.

First, a rectangular scanning region image R' is displayed, and at the same time, the cross-sectional-position information T1 and T2 that indicates two cross-sectional positions specified in Step S9 are displayed on the observation position image GP of the fundus oculi observation display 1000 in FIG. 12. The cross-sectional-position information Ti is a linear image that indicates the cross-sectional position laterally (x direction shown in FIG. 1 or the like) on the fundus oculi observation display 1000. In addition, the cross-sectional-position information T2 is a linear image that indicates the cross-sectional position along the longitudinal direction (y direction) on the fundus oculi observation display 1000. Moreover, the intersection point of the cross-sectional position information T1 and T2 is equivalent to the single point designated in Step S8. In other words, the cross-sectional-position information T1 and T2 represents a cruciform cross-sectional position that intersects at a single point.

The rectangular scanning region image R' is displayed as described above, and at the same time, the cross-sectional-position information t1 and t2 that indicate two cross-sectional positions specified in Step S9 are displayed on the color image Ef'. The cross-sectional-position information t1 and t2 consists of an arrow-shaped image displayed outside the scanning region image R'. The lateral cross-sectional position is provided at a position linking a pair of cross-sectional-position information t1. In addition, the longitudinal cross-sectional position is provided at a position linking a pair of cross-sectional-position information t2. Incidentally, the objective of displaying the cross-sectional-position information t1 and t2 outside the scanning region image R' is to not disturb the observation of images in the scanning region image R'.

The scanning region image R and the cross-sectional-position information t1 and t2, which are similar to those on the color image Ef', are displayed also on each of the fluorescence images GF and GI.

The intersecting-position specifying part 216 specifies the intersecting position of the two cross-sectional positions specified in Step S9, that is to say, the position of the single point designated in Step S8 (x coordinate value and y coordinate value) (S11).

When the examiner performs a predetermined operation (such as pressing the imaging switch 306) (S12), the fundus oculi observation device 1 obtains a tomographic image of the fundus oculi Ef along each cross-sectional position specified in Step S9 (S13). At this time, the signal lights LS are scanned along each of the cross-sectional positions, thereby forming a tomographic image. Image data of the obtained tomographic image is stored on the storage 212 of the arithmetic and control unit 200 along with the imaging information or the like.

The main controller 211 displays, on the tomographic image display part 1005, a tomographic image GT1 along the cross-sectional position laterally obtained in Step S13, and displays, on the tomographic image display part 1006, a tomographic image GT2 along the cross-sectional position in the longitudinal direction (S14). This results in displaying, on the fundus oculi observation display 1000, the color image Ef', the fluorescence images GF and GI, and the tomographic images GT1 and GT2 of the fundus oculi Ef.

Furthermore, the main controller 211 displays, on each of the tomographic images GT1 and GT2, intersecting position information C that indicates the intersecting position specified in Step S11 (S15). This intersecting position information C is a linear image that extends in the depth direction (z direction) of the fundus oculi Ef.

The examiner can observe the fundus oculi Ef while changing the cross-sectional position by changing the imaging mode of Step S5, the scanning region R of Step S6, the designated position of Step S8, etc., accordingly. This concludes the explanation of this aspect of usage.

Second Aspect of Usage

Figure 13:
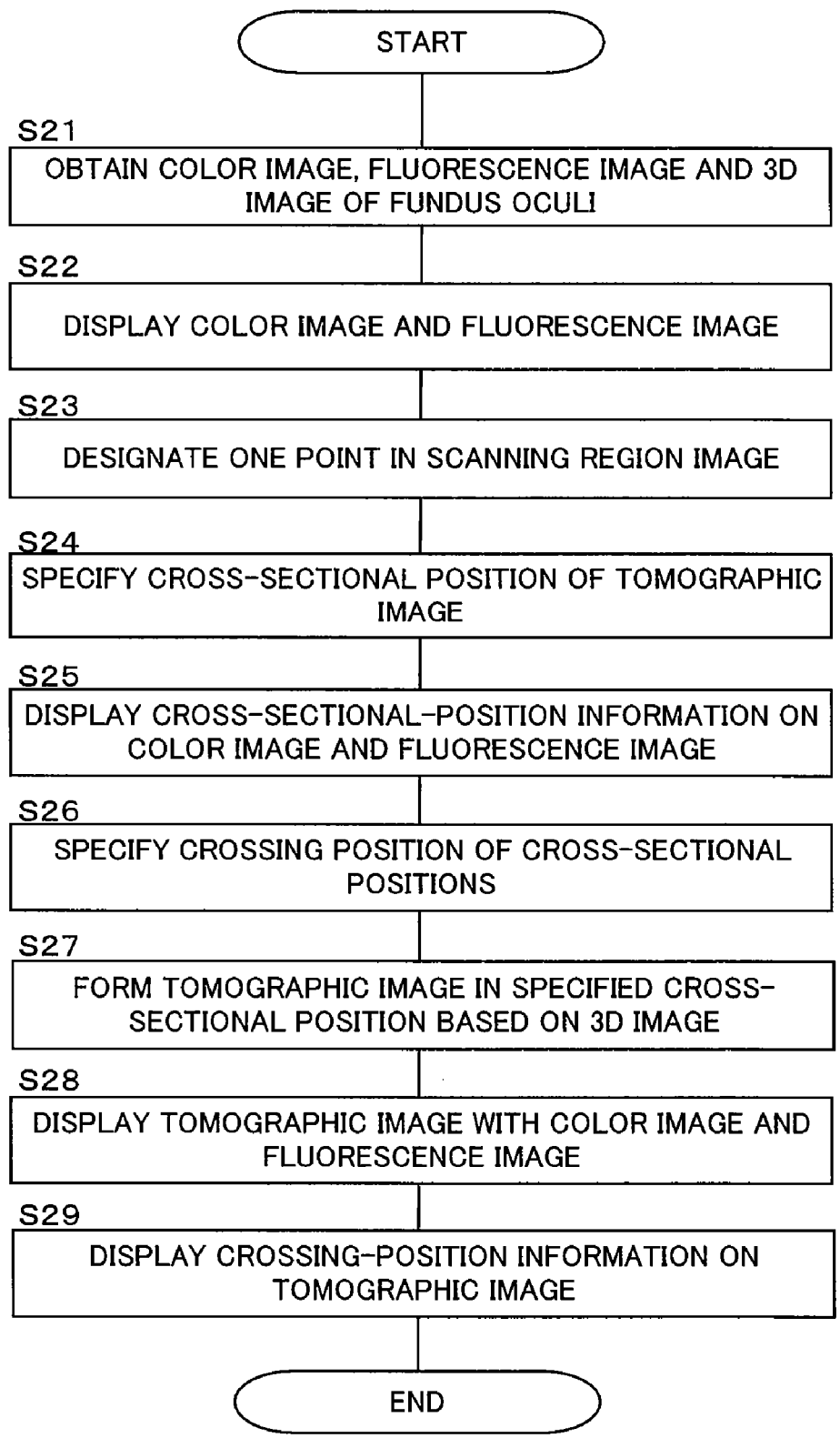
FIG. 13 is a flowchart showing one example of the usage mode of the preferred embodiment of the fundus oculi observation device according to the present invention.

A case of observation while obtaining a tomographic image of the fundus oculi Ef has been explained in the above first aspect of usage, but the fundus oculi observation device 1 can also be used for observation after obtaining a color image, a fluorescence image, and a tomographic image (3D image). In that case, it is desirable to obtain a 3D image of the fundus oculi Ef by means of the abovementioned 1-sec imaging mode or 3-sec imaging mode. FIG. 13 shows an example of such an aspect of usage.

A color image, a fluorescence image, and a 3D image of the fundus oculi Ef are obtained in advance (S21). Image data of the obtained images is stored on the storage 212 along with the imaging information or the like.

When the examiner performs a predetermined operation, the main controller 211 reads the image data of the color image and the fluorescence image from the storage 211 and displays the same on the display 240A (S22). Consequently, the color image Ef' and the fluorescence images GF and GI are displayed on the fundus oculi observation display 1000, as shown for example in FIG. 11. Incidentally, at this time, the display size or position of images may be adjusted, as is the case with the above aspect of usage (Step S3). Alternatively, a scale image, depending on the display size of each of images Ef', GF, and GI, may be displayed.

In this aspect of usage, a 3D image of the fundus oculi Ef has already been obtained, so a scanning region image R', which corresponds to the scanning region R at the time when obtaining this 3D image, is displayed on each of the color image Ef' and the fluorescence images GF and GI.

When the examiner then designates a single point in the scanning region image R' on the color image Ef' and the fluorescence image GF and GI (S23), the cross-sectional-position designating part 213 specifies, for each of the color image Ef' and the fluorescence images GF and GI, two cruciform cross-sectional positions that intersect at a single point (S24). Incidentally, the cross-sectional position is not limited to a cruciform.

The main controller 211 displays, as is the case for example with FIG. 12, the cross-sectional-position information t1 and t2 that represent the specified cross-sectional positions, overlapping each of the color image Ef' and the fluorescence images GF and GI (S25). At this time, the cross-sectional-position information T1 and T2 is displayed also on the observation position image GP.

The intersecting-position specifying part 216 specifies the intersecting position of the two cross-sectional positions specified in Step S24 (S26).

In addition, the image processor 230 forms, based on the image data of the 3D image, (image data of) the tomographic images GT1 and GT2 along each of the cross-sectional positions specified in Step S24 (S27).

The main controller 211 displays, on the fundus oculi observation display 1000, tomographic images GT1 and GT2 along with the color image Ef' and the fluorescence images GF and GI (S28), and displays, on the each of the tomographic images GT1 and GT2, intersecting position information C that indicates the intersecting position specified in Step S26 (S29).

The examiner can observe the fundus oculi Ef while changing the cross-sectional position by changing the designated position of Step S23 or the like accordingly. This is the end of the explanation of this aspect of usage.

Third Aspect of Usage

Figure 14:
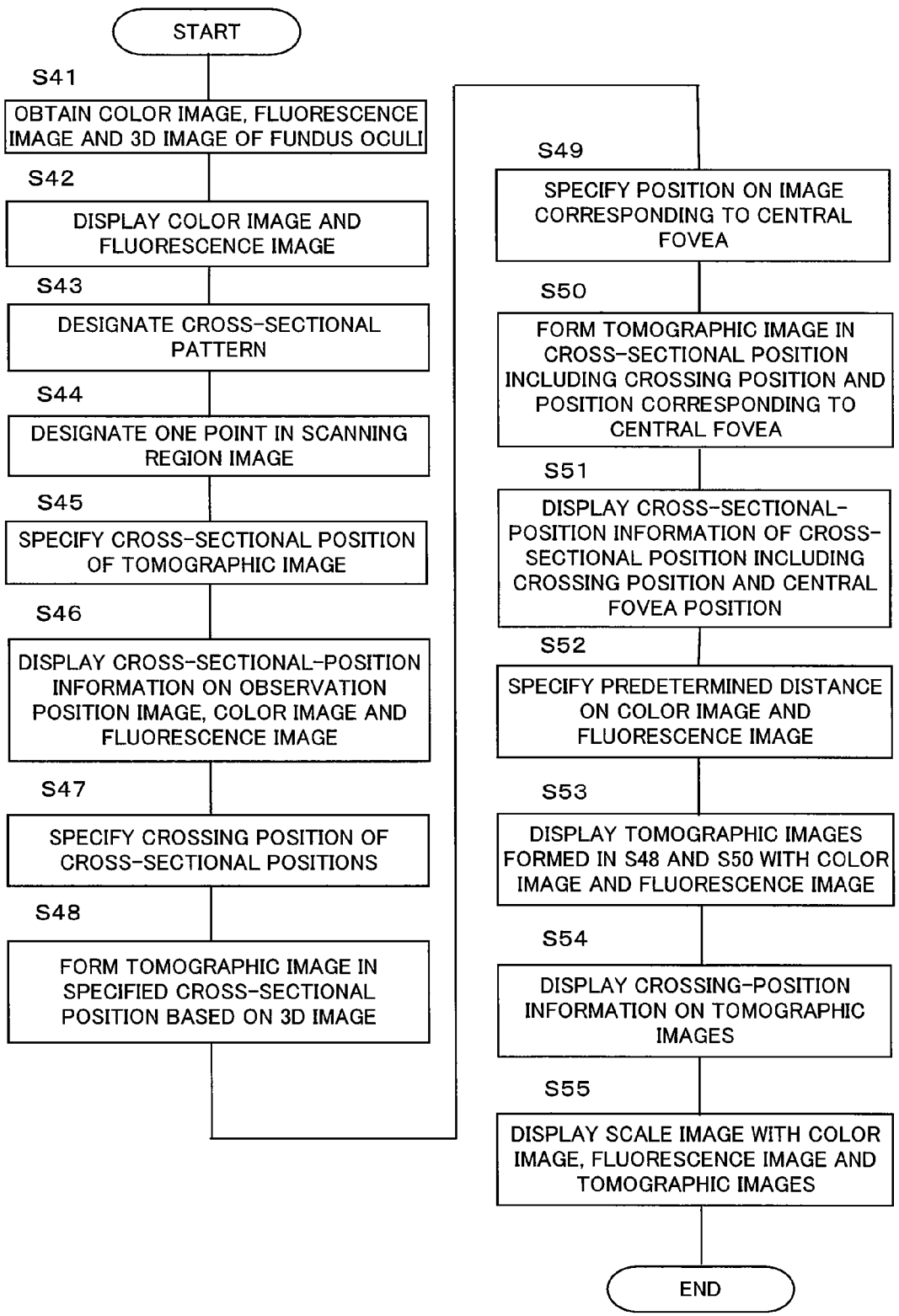
FIG. 14 is a flowchart showing one example of the usage mode of the preferred embodiment of the fundus oculi observation device according to the present invention.
Figure 15:
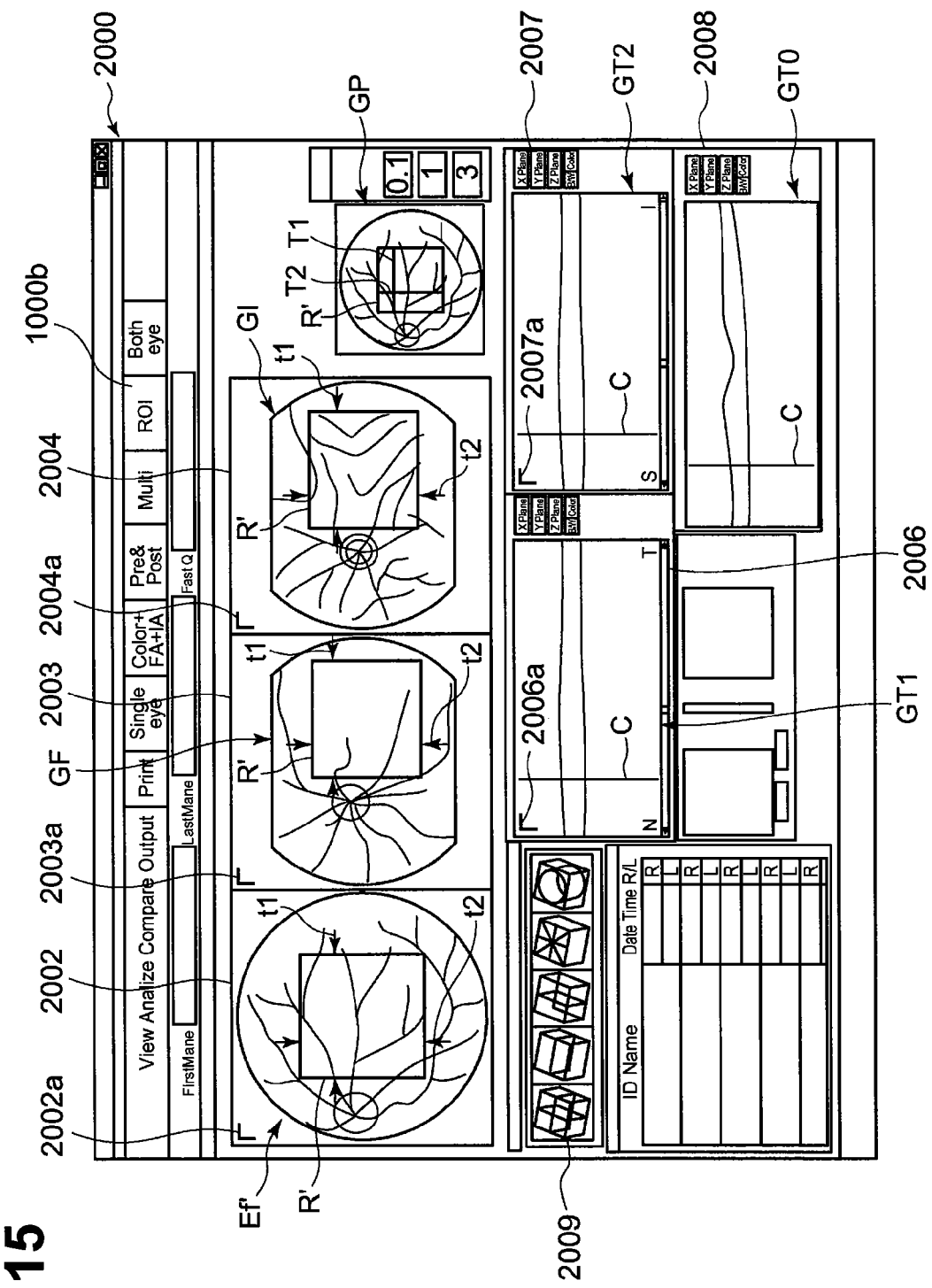
FIG. 15 is a schematic diagram showing one example of a display screen displayed in a preferred embodiment of the fundus oculi observation device according to the present invention.

A third aspect of usage is the aspect of using the fundus oculi observation display 1000 in FIG. 11 when the second designation button 1000b is clicked. FIG. 14 is a flowchart that shows an example of this aspect of usage. In addition, FIG. 15 shows an example of a screen displayed when the second designation button 1000b is clicked.

Incidentally, a case of observation after obtaining a color image, a fluorescence image, and a tomographic image (3D image) is explained in this aspect of usage, but the case of observation while obtaining a tomographic image of the fundus oculi Ef can also be implemented, as is the case with the first aspect of usage.

A color image, a fluorescence image, fluorescence images (a fluoresce in fluorescence image and an indocyanine green fluorescence image), and a 3D image of the fundus oculi Ef are obtained in advance (S41). Image data of the obtained images is stored on the storage 212 along with the imaging information or the like.

When the examiner performs a predetermined operation, the main controller 211 reads the image data of the color image, and the fluorescence images from the storage 211 and displays them on the display 240A (S42).

The color image is displayed on the color image display part 2002 of the fundus oculi observation display 2000, as shown in FIG. 15 (cf. the color image Ef' in FIG. 15). A scanning region image R', which corresponds to the scanning region R at the time of obtaining this 3D image, is displayed on this color image Ef'.

In addition, the fluorescein fluorescence image and the indocyanine green fluorescence image are displayed, as shown in FIG. 15, on the fluorescence image display parts 2003 and 2004, respectively (cf. the fluorescence images GF and GI in FIG. 15). A scanning region image R' is displayed on each of the fluorescence images GF and GI. Incidentally, the observation position image GP and the scanning region image are displayed also on the observation position image display part 2001.

Incidentally, in this phase, the cross-sectional-position information t1 or t2 or the tomographic image GT1, GT2, or GT0 in FIG. 15 are not to be displayed yet.

Next, the examiner designates a cross-sectional pattern of the tomographic image to be observed (morphology of the cross-sectional position) (S43).

The fundus oculi observation display 2000 is provided with a cross-sectional-pattern designating part 2009 having buttons of options for various cross-sectional patterns. Buttons for designating, in order from the left side of the paper, a cruciform pattern, a linear lateral pattern, a linear longitudinal pattern, a radial pattern, and a circular cross-sectional pattern are arranged on the cross-sectional-pattern designating part 2009. Incidentally, it may be configured so as to be capable of setting an optional cross-sectional pattern such as by the drag operation of a mouse 206 (In other words, a button for designating a free-form cross-sectional pattern may be provided).

The examiner designates the cross-sectional pattern by clicking a desired button of the cross-sectional-pattern designating part 2009 with the mouse 206. In this aspect of usage, a case in which the cruciform cross-sectional pattern has been designated will be explained.

The examiner then designates a single point in the scanning region image R' on the color image Ef' (or the fluorescence image GF or GI) (S44). The cross-sectional-position designating part 213 specifies, for each of the color image Ef' and the fluorescence images GF and GI, two cruciform cross-sectional positions that intersect each other at a single designated point (S45).

As shown in FIG. 15, the main controller 211 displays, on the observation position image GP, cross-sectional-position information T1 and T2 that represents the specified cross-sectional positions, and displays cross-sectional-position information t1 and t2 that represents the cross-sectional positions, overlapping the color image Ef' and the fluorescence images GF and GI (S46).

The intersecting-position specifying part 216 specifies the intersecting position of the two cross-sectional positions specified in Step S45 (S47).

In addition, the image processor 230 forms, based on the image data of the 3D image, image data of the tomographic images GT1 and GT2 along each of the cross-sectional positions specified in Step S45 (S48).

Moreover, the image processor 230 specifies a position that is equivalent to the fovea centralis of the fundus oculi Ef in the image (assuming the color image Ef') in which a single point has been designated in Step S44 (S49).

This process will be explained. The fovea centralis is generally equivalent to the thinnest part of the retina. The image processor 230 specifies the position of the fovea centralis on the color image Ef' by detecting the position (x coordinate value, y coordinate value) of the thinnest part of the retina by analyzing the 3D image that has been obtained in Step S41, and by specifying the position on the color image Ef' corresponding to this detected position.

At this time, taking the thickness of the periphery of the thinnest part of the retina into account enables improvement of detection accuracy. In other words, changes in the thickness of the periphery of an affected area are relatively rapid and changes in the thickness of the periphery of the fovea centralis are relatively modest, so the fovea centralis and the affected area can be distinguished.

The detection of the fovea centralis by means of the thickness of the retina described above can be achieved, for example, as follows. First, a region in a tomographic image equivalent to the surface of the retina, such as the boundary position between the retina and a corpus vitreum or the inner limiting membrane of the retina (first region) and a region in a tomographic image equivalent to a predetermined layer of the retina, such as a pigment layer of the retina (second region) are each specified by analyzing a 3D image. Next, for each site (each x-y coordinate position) of this 3D image, the distance in the z direction of the first region and the second region is arithmetically calculated. Then, a site (x coordinate value, y coordinate value) in which this distance is the minimum value is found, considering the site as a position equivalent to the fovea centralis.

Incidentally, when attempting to improve the detection accuracy of the position of the fovea centralis as described above, a site in which the abovementioned distance is equal to or more than a predetermined value and is the minimal value is specified (sometimes a plurality of sites are specified), and changes in the abovementioned distance in the periphery of the specified each site are found (e.g., a differential coefficient is arithmetically calculated). The predetermined value is set in advance, for example, based on clinical data of the depth of the fovea centralis or the like. A site in which the degree of changes in the abovementioned distance is equal to or less than a threshold is then regarded as a position equivalent to the fovea centralis. Herein, a site in which changes in the abovementioned distance is the minimum (i.e., a site in which changes are the most modest) may also be regarded as the position equivalent to the fovea centralis. Incidentally, the threshold is set in advance, based on clinical data of morphology of the periphery of the fovea centralis or the like.

The position of the fovea centralis may also be specified in a pre-measurement at an alignment before performing Step S1. In addition, in Step S49, the examiner may visually search the position of the fovea centralis on the color image Ef' and may designate the position using a mouse 206, for example, instead of automatically detecting the fovea centralis. Moreover, it is adapted so that the position of the fovea centralis automatically detected in Step S49 can be corrected such as by the mouse 206. In that case, it is desirable to display, on the color image Ef', the position of the fovea centralis that has been automatically detected.

The image processor 230 forms, based on the image data of the 3D image, image data of the tomographic image GT0 along the cross-sectional position that includes a line segment linking the intersecting position specified in Step S47 to the position of the fovea centralis specified in Step S49 (S50).

The main controller 211 displays, on the observation position image GP, cross-sectional-position information T0 that represents the cross-sectional position of the tomographic image GT0, as shown in FIG. 15 (S51). At this time, the cross-sectional-position information of the tomographic image GT0 may be displayed also on the color image Ef and the fluorescence images GF and GI.

In addition, the scale-specifying part 214 specifies a predetermined distance in each of the color image Ef' and the fluorescence images GF and GI (S52).

The main controller 211 displays, on the fundus oculi observation display 2000, tomographic images GT1, GT2, and GT0 along with the color image Ef' and the fluorescence images GF and GI (S53). At this time, as shown in FIG. 15, the tomographic images GT1, GT2, and GT0 are displayed on the tomographic image display parts 2006, 2007, and 2008, respectively.

In addition, the main controller 211 displays, on each of the tomographic images GT1 and GT2, intersecting position information C that indicates the intersecting position specified in Step S47 (S54). At this time, the intersecting position information may be displayed also on the tomographic image GT0. Moreover, it is also possible to display, on the tomographic image GT0, information that indicates a position equivalent to the fovea centralis.

Furthermore, the main controller 211 displays scale images 2002a, 2003a, and 2004a that are based on the predetermined distance specified in Step S52, along with the color image Ef' and the fluorescence images GF and GI, respectively (S55).

The examiner can observe the fundus oculi Ef while changing the cross-sectional position by changing the cross-sectional pattern of Step S43, the designated position of Step S44, etc., accordingly. This concludes the explanation of this aspect of usage. Incidentally, the fovea centralis is basically a fixation point in fundus oculi observation, so it may be adapted to find the position equivalent to the fovea centralis from a presentation position of the fixation target in the measurement range. This method has the advantage of being easy, but accuracy is low.

Actions and Advantageous Effects

The actions and advantageous effects of the aforementioned fundus observation device 1 will be described.

This fundus oculi observation device 1 acts so as to form a color image (that is equivalent to the "2D image of the surface of the fundus oculi" includes the fundus oculi observation image GP and includes a monochrome image), a fluorescence image, and a tomographic image of the fundus oculi Ef, to display the color image, the fluorescence image, and the tomographic image side by side, and to display the cross-sectional-position information that represents the cross-sectional position of the tomographic image so as to overlap the color image or the fluorescence image.

The fluorescence image is an image that represents the condition of the surface of the fundus oculi Ef or the vicinity thereof (particularly, the condition of blood vessels). In addition, the tomographic image is an image that represents the condition of a cross section spanning from the surface of the fundus oculi Ef to deeper tissues. Therefore, according to this fundus oculi observation device 1, the examiner can observe both the fluorescence image and the tomographic image simultaneously and can ascertain the positional relationship between the fluorescence image and the tomographic image, and can thereby ascertain, in detail, the condition of the surface of the fundus oculi and the vicinity thereof as well as the condition of deeper tissues.

In addition, according to this fundus oculi observation device 1, it is possible to observe the condition of an identical site of the fundus oculi Ef by means of different types of images, thereby enabling a more composite and comprehensive diagnosis.

Moreover, with the fundus oculi observation device 1, a color image of the fundus oculi can be displayed simultaneously in addition to a fluorescence image and tomographic image, so it is possible to ascertain in greater detail the condition of the surface of the fundus oculi and the vicinity thereof as well as deeper tissues of the fundus oculi.

In addition, with the fundus oculi observation device 1, the examiner can designate a cross-sectional pattern of a tomographic image. The fundus oculi observation device 1 acts so as to form a tomographic image, based on the designated cross-sectional pattern, to display the tomographic image next to a fluorescence image or a color image, and to display the cross-sectional-position information of the tomographic image overlapping the fluorescence image or the color image.

Consequently, the examiner can observe, along with the fluorescence image or the color image, a tomographic image that is based on a desired cross-sectional pattern, and can further ascertain the cross-sectional position of the tomographic image on the fluorescence image or the color image. Therefore, it is possible to ascertain, in detail, the condition of the surface of the fundus oculi and the vicinity thereof, and further detail of a desired site of deeper tissues.

Moreover, with the fundus oculi observation device 1, when the designated cross-sectional pattern has two or more cross-sectional positions that intersect each other (e.g., a case of a cruciform cross-sectional position), it is possible to display the intersecting position information that represents this intersecting position overlapping each of the tomographic images, thereby enabling the examiner to easily ascertain the intersecting position of a tomographic image and a tomographic image.

In addition, with the fundus oculi observation device 1, the examiner can designate a desired cross-sectional position on a fluorescence image or a color image. The fundus oculi observation device 1 acts so as to form a tomographic image at the designated cross-sectional position, to display the tomographic image next to a fluorescence image or a color image, and to display the cross-sectional-position information of the tomographic image overlapping the fluorescence image or the color image.

Consequently, the examiner can observe, along with the fluorescence image or the color image, a tomographic image that is based on a desired cross-sectional position, and can further ascertain the cross-sectional position of the tomographic image on the fluorescence image or the color image. Therefore, it is possible to ascertain, in detail, the condition of the surface of the fundus oculi and the vicinity thereof, and further detail of a desired site of deeper tissues.

Incidentally, in this embodiment, when designating a single point on a fluorescence image or a color image, the cross-sectional position of a predetermined cross-sectional pattern passing through the single point (particularly, a cruciform cross-sectional pattern has been explained) will be designated, but it is also possible to directly designate the cross-sectional position by employing the mouse 206 or the like as in the case of designating the free-form cross-sectional position in the third aspect of usage.

Furthermore, with the fundus oculi observation device 1, it is possible to form a tomographic image at the cross-sectional position that includes a single point on the designated cross-sectional position and a single point on a fluorescence image or a color image that is equivalent to the fovea centralis of the fundus oculi, and to display this tomographic image next to the fluorescence image or the color image. In addition, it is possible to display, on the observation position image GP, the cross-sectional-position information T0 that represents the cross-sectional position of this tomographic image.

Visual information obtained by the fovea centralis is known to account for approximately half of the visual information obtained by an eye. In addition, a site on which fundus oculi observation focuses (cross-sectional position, particularly, the abovementioned a single point) is generally an affected area. Therefore, it is extremely important in diagnosis to ascertain the positional relationship between the fovea centralis and the affected area and the condition of the fundus oculi Ef between them. According to this fundus oculi observation device 1, the examiner can observe a tomographic image of the cross section including the site of interest and the fovea centralis along with a fluorescence image or a color image, thereby enabling the facilitation of diagnosis, improvement of the accuracy of diagnosis, etc. In addition, the examiner can easily ascertain the positional relationship between the site of interest and the fovea centralis and the cross-sectional position of the tomographic image by the cross-sectional-position information T0.

In addition, with the fundus oculi observation device 1, it is possible to display a scale image that represents a predetermined distance on an image along with a fluorescence image or a color image, thereby enabling the examiner to easily ascertain the difference in size between the images.

Incidentally, although omitted in this embodiment, it is also possible to display a scale image along with a tomographic image. This enables the examiner to easily ascertain the difference in size between two or more tomographic images or the difference in size between a tomographic image and a color image or a fluorescence image.

In addition, with the fundus oculi observation device 1, it is possible to adjust the display size of a fluorescence image and a color image to each other and to display them next to a tomographic image, thereby enabling the examiner to easily ascertain the positional relationship between the fluorescence image and the color image that have been imaged from the same direction.

Modification

The configuration described above is merely one example to preferably implement the fundus oculi observation device according to the present invention. Therefore, any modification may be implemented appropriately within the scope of the present invention.

The fundus oculi observation device capable of each forming a color image, a fluorescence image, and a tomographic image has been explained in the embodiment above, but the fundus oculi observation device according to the present invention is sufficient if it is capable of forming a fluorescence image and a tomographic image.

In addition, the fundus oculi observation device of the above embodiment is capable of forming both a fluorescein fluorescence image and an indocyanine green fluorescence image as fluorescence images, but the fundus oculi observation device according to the present invention only has to be capable of forming at least one of these.

The fundus oculi observation device according to the present invention can be configured to be capable of switching display images accordingly. For example, it can be configured to be capable of selectively displaying a desired image from among a color image, a fluorescein fluorescence image, an indocyanine green fluorescence image, and a tomographic image by operating an image-switching switch 308 on the operation panel 3a, a soft key on the display screen, etc. In addition, it is also possible to configure so to be able to selectively display a desired tomographic image with the similar operation when two or more tomographic images have been obtained. Incidentally, when selectively displaying an image, it is desirable to expand the display size of the image to be displayed. Such a configuration makes it possible to observe only the necessary images accordingly.

In addition, when the display size and position have been adjusted among two or more images, it is possible to display these images by superimposing on one another. For example, it is possible to display a color image and a fluorescence image overlapping each other, or to display a fluorescein fluorescence image and an indocyanine green fluorescence image overlapping each other. At this time, an image to be overlap another is converted to semi-transparent and is superimposed on the other image. Incidentally, it is also possible to display three or more images overlapping each other.

In the embodiment above, a configuration for forming and displaying a tomographic image that has a cross section including a single point of a linear scanning line (cross-sectional position) and a position equivalent to the fovea centralis has been explained. When obtaining a tomographic image such as of a glaucomatous eye, the signal light LS can be scanned along a circular scanning line, and a tomographic image along this scanning line (cross-sectional position) can be formed and displayed. In that case, the examiner selects the circular scanning line (cross-sectional pattern) by operating a button on the right edge of the cross-sectional-pattern designating part 2009 in FIG. 15. The fundus oculi observation device 1 is operated so as to form and display a tomographic image that has a cross section, including the center position of this circular scanning line and a position equivalent to the fovea centralis.

Moreover, when displaying an internal fixation target at the fixation position for imaging the macula flava (described above) by means of the fixation target-switching switch 309 of the operation panel 3a, the fovea centralis will be located almost at the middle of the image to be obtained. In that case, it can be configured so as to form and display a tomographic image that has a cross section including a single point on the image designated by the examiner (site of interest) and the middle position.

Moreover, it is possible to provide an imaging mode for forming and displaying only a tomographic image of a cross section that includes a site of interest such as an affected area and a position equivalent to the fovea centralis. Consequently, it is possible to perform imaging within the minimum necessary time period, enabling a reduction in imaging time and improvement of the imaging success rate.

In addition, in the embodiment above, the fundus oculi observation device obtains all images to be subject to fundus oculi observation, but the device may receive and display an image that has been imaged by another fundus oculi imaging device. For example, it is possible to configure so as to display image data of a fluorescence image that has been separately imaged by a mydriatic retinal camera, through acquisition via a network such as a LAN or a storage media such as a DVD. Consequently, it is possible to make a more composite diagnosis, including images that have been imaged by other devices.

Moreover, more medical agencies have utilized an image database for storing image data of imaged images in recent years. In that case, it can be configured so as to obtain image data of a desired image from the image database via a network accordingly and display the same. Consequently, it is possible to perform a more composite diagnosis with reference to the images stored in the image database. In particular, it is possible to reference images that have been imaged in the past, thereby making it convenient for an observation of the clinical course or the like.

In addition, when the examiner designates the cross-sectional position on a color image or fluorescence image displayed on the fundus oculi observation device, it is possible to configure so as to specify the cross-sectional position for each of the images of the eye that is stored in the image database. Consequently, in an observation of the clinical course for example, when designating the cross-sectional position on an image that has been imaged on a certain date and time, the cross-sectional position will be designated also on an image that has been imaged on another date and time, so it is possible to easily and promptly perform a comparative observation of tomographic images with the same cross-sectional position.

Moreover, the fundus oculi observation device 1 of the above embodiment is a Fourier domain OCT device, but the configuration of the present invention can also be applied to a time domain OCT device. Incidentally, a time domain OCT device is described, for example, such as in Japanese Unexamined Patent Application Publication 2005-241464 filed by the present applicant.

Fundus Oculi Image Display Device

A fundus oculi image display device according to the present invention will be explained. Incidentally, in the embodiments above, the arithmetic and control unit 200 is employed as the fundus oculi image display device.

The fundus oculi image display device according to the present invention comprises a storage for storing a fluorescence image and a tomographic image of the fundus oculi of an eye, a display part, and a controller.

The fluorescence image and the tomographic image are obtained by an external retinal camera or optical image measurement device. The fluorescence image and the tomographic image may be stored in an image database on a network. The fundus oculi image display device receives input of the fluorescence image and the tomographic image via a network or a storage media, and stores the input image on the storage.

The controller acts to display side-by-side, on the display part, the fluorescence image and the tomographic image that have been stored on the storage, and to display the cross-sectional-position information that represents the cross-sectional position of the tomographic image on the fluorescence image overlapping the fluorescence image.

According to such a fundus oculi image display device, the examiner can observe both the fluorescence image and the tomographic image simultaneously, can further ascertain the positional relationship between the fluorescence image and the tomographic image, and can thereby ascertain, in detail, the condition of the surface of the fundus oculi and the vicinity thereof as well as the condition of deeper tissues. In addition, it is possible to observe the condition of an identical site of the fundus oculi by means of different types of images, thereby enabling more composite and comprehensive diagnosis.

Incidentally, the fundus oculi image display device according to the present invention may incorporate the optional functions of the arithmetic and control unit 200 of the above embodiment.

Program

A program used in the present invention will be explained hereunder. In the above embodiments, the control program 204*a* is equivalent to the program.

The program used in the present invention is a computer program for making a computer, which comprises a storage and a display part, function as the above fundus oculi image display device (regarding the function, see the description in the above FUNDUS IMAGE DISPLAY DEVICE).

The program used in the present invention can be recorded in any recording medium readable by a drive of the computer. For example, a recording medium such as an optical disk, a magneto-optical disk (CD-ROM, DVD-ROM, DVD-ROM, MO, etc.) and a magnetic storage medium (hard disk, floppy disk™, ZIP, etc.) can be used. Moreover, it is also possible to store the program in a storage device such as a hard disk drive or a memory. Furthermore, it is also possible to transmit the program via a network such as the Internet and a LAN.

What is claimed is:

1. A fundus oculi observation device, comprising:
a first image forming part configured to optically obtain data and, based on the obtained data, form a fluorescence image of a fundus oculi of an eye administered with a fluorescent agent in advance and a 2D image of a surface of the fluids oculi;
a second image forming part configured to optically obtain data and, based on the obtained data, form a tomographic image of the fundus oculi;
a display part; and
a controller configured to cause the display part to display the 2D image and the fluorescence image formed by the first image forming part side by side with the tomographic image formed by the second image forming part, and to cause the display part to display cross-sectional-position information that represents a relation between a position on the tomographic image and a common position on the 2D image and the fluorescence image.

2. The fundus oculi observation device according to claim 1, wherein the first image forming part forms a fluorescein fluorescence image as the fluorescence image.

3. The fundus oculi observation device according to claim 1, wherein the first image forming part forms an indocyanine green fluorescence image as the fluorescence image.

4. The fundus oculi observation device according to claim 1, further comprising:
a cross-sectional-pattern designating part configured to designate a cross-sectional pattern of a tomographic image of a fundus oculi, wherein:
the second image forming part forms one or more tomographic images based on the designated cross-sectional pattern; and
the controller causes the formed one or more tomographic images to be displayed side by side with the fluorescence image, and causes the cross-sectional-position information of each of the one or more tomographic images to be displayed so as to overlap the fluorescence image.

5. The fundus oculi observation device according to claim 4, wherein the controller, in the case in which a cross-sectional pattern designated by the cross-sectional-pattern designating part has two or more cross-sectional positions that mutually cross, causes crossing-position information representing the crossing position to be displayed so as to overlap each of the tomographic images of the two or more cross-sectional positions.

6. The fundus oculi observation device according to claim 1, further comprising:
a cross-sectional-position designating part configured to designate a cross-sectional position on the displayed fluorescence image;
wherein the second image forming part forms the tomographic image in the designated cross-sectional position.

7. The fundus oculi observation device according to claim 6, wherein:
the second image forming part forms a new tomographic image in a cross-sectional position including a point on a cross-sectional position designated by the cross-sectional-position designating part, and a point on the fluorescence image equivalent to a fovea centralis of the fundus oculi; and
the controller causes the newly formed tomographic image to be displayed side by side with the fluorescence image.

8. The fundus oculi observation device according to claim 1, wherein the controller causes a scale image representing a distance on the displayed fluorescence image and/or on the displayed tomographic image, to be displayed with the fluorescence image and/or the tomographic image.

9. The fundus oculi observation device according to claim 1, wherein:
the first image forming part optically obtains data, and further forms a 2D image of a surface of the fundus oculi based on the obtained data; and
the controller causes the display part to display the formed 2D image side by side with the fluorescence image and the tomographic image, and display cross-sectional-position information that represents a cross-sectional position of the tomographic image in the 2D image so as to overlap the 2D image.

10. The fundus oculi observation device according to claim 9, further comprising:
a cross-sectional-pattern designating part configured to designate a cross-sectional pattern of a tomographic image of a fundus oculi, wherein:
the second image forming part forms one or more tomographic images based on the designated cross-sectional pattern; and the controller causes the formed one or more tomographic images to be displayed side-by-side with the fluorescence image and the 2D image, and causes the cross-sectional-position information of each of the one or more tomographic images, to be displayed so as to overlap each of the fluorescence image and the 2D image.

11. The fundus oculi observation device according to claim 10, wherein the controller, in the case in which a cross-sectional pattern designated by the cross-sectional-pattern designating part has two or more cross-sectional positions that mutually cross, causes crossing-position information representing the crossing position to be displayed so as to overlap each of the tomographic images of the two or more cross-sectional positions.

12. The fundus oculi observation device according to claim 9, further comprising:
a cross-sectional-position designating part configured to designate a cross-sectional position on the displayed 2D image,
wherein the second image forming part forms the tomographic image in the designated cross-sectional position.

13. The fundus oculi observation device according to claim 12, wherein:
the second image forming part forms a new tomographic image in a cross-sectional position including a point on a cross-sectional position designated by the cross-sectional-position designating part, and a point on the 2D image corresponding to a central fossa of the fundus oculi; and
the controller causes the newly formed tomographic image to be displayed side by side with the 2D image.

14. The fundus oculi observation device according to claim 9, wherein the controller causes a scale image representing a distance on the displayed fluorescence image, the displayed tomographic image, and/or the displayed 2D image, to be displayed with the fluorescence image, the tomographic image, and/or the 2D image.

15. The fundus oculi observation device according to claim 9, wherein the controller comprises a display-size-changing part configured to match a display size between the fluorescence image and the 2D image, and causes the fluorescence image and the 2D image whose display sizes are matched, to be displayed side by side with the tomographic image.

* * * * *